US010640809B2

(12) United States Patent
Kuersten et al.

(10) Patent No.: US 10,640,809 B2
(45) Date of Patent: May 5, 2020

(54) METHODS OF ANALYZING NUCLEIC ACIDS

(71) Applicant: EPICENTRE TECHNOLOGIES CORPORATION, Madison, WI (US)

(72) Inventors: Scott Kuersten, Madison, WI (US); Agnes Radek, Madison, WI (US); Ramesh Vaidyanathan, Madison, WI (US); Haiying Li Grunenwald, Madison, WI (US)

(73) Assignee: EPICENTRE TECHNOLOGIES CORPORATION, Madison, WI (US)

( * ) Notice: Subject to any disclaimer, the term of this patent is extended or adjusted under 35 U.S.C. 154(b) by 220 days.

(21) Appl. No.: 15/576,382

(22) PCT Filed: May 27, 2016

(86) PCT No.: PCT/US2016/034809
§ 371 (c)(1),
(2) Date: Nov. 22, 2017

(87) PCT Pub. No.: WO2016/196358
PCT Pub. Date: Dec. 8, 2016

(65) Prior Publication Data
US 2018/0148767 A1 May 31, 2018

Related U.S. Application Data

(60) Provisional application No. 62/168,281, filed on May 29, 2015.

(51) Int. Cl.
*C12Q 1/6806* (2018.01)
*C12N 15/10* (2006.01)
*C12Q 1/6874* (2018.01)

(52) U.S. Cl.
CPC ....... *C12Q 1/6806* (2013.01); *C12N 15/1096* (2013.01); *C12Q 1/6874* (2013.01)

(58) Field of Classification Search
CPC .................................................. C12Q 1/6806
USPC ......................................................... 506/16
See application file for complete search history.

(56) References Cited

U.S. PATENT DOCUMENTS

| | | | |
|---|---|---|---|
| 5,925,545 A | 7/1999 | Reznikoff et al. | |
| 5,965,443 A | 10/1999 | Reznikoff et al. | |
| 6,083,695 A * | 7/2000 | Hardin | C12Q 1/6869 435/6.11 |
| 7,083,980 B2 | 8/2006 | Reznikoff et al. | |
| 7,435,794 B2 | 10/2008 | Lukyanov et al. | |
| 7,608,434 B2 | 10/2009 | Reznikoff et al. | |
| 7,803,922 B2 | 9/2010 | Lukyanov et al. | |
| 2004/0185484 A1* | 9/2004 | Costa | B01L 3/502707 506/14 |
| 2005/0153333 A1 | 7/2005 | Sooknanan | |
| 2009/0026082 A1* | 1/2009 | Rothberg | C12Q 1/6869 204/556 |
| 2010/0297643 A1 | 11/2010 | Sooknanan | |
| 2014/0194324 A1 | 7/2014 | Gormley et al. | |
| 2015/0291942 A1 | 10/2015 | Gloeckner et al. | |

FOREIGN PATENT DOCUMENTS

| | | |
|---|---|---|
| WO | WO 95/23875 A1 | 9/1995 |
| WO | WO 2010/048605 A1 | 4/2010 |
| WO | WO 2012/061832 A1 | 5/2012 |
| WO | WO 2012/108864 A1 | 8/2012 |
| WO | WO 2014/108810 A2 | 7/2014 |
| WO | WO 2015/049278 A1 | 4/2015 |
| WO | WO 2015/160895 A2 | 10/2015 |

OTHER PUBLICATIONS

Vaidyanathan, et al., "R&DNA-Seq: Sequencing the genome and transcriptome from the same cell", poster from CSHL 2011.
International Search Report and Written Opinion for PCT/US2016/034809, dated Aug. 31, 2016, 15 pages.
Bogdanova et al., "Normalization of full-length enriched cDNA," *Molecular BioSystems*, Jan. 2008; 4(3):205-212.
Gijavanekar et al., "Rare target enrichment for ultrasensitive PCR detection using cot-rehybridization and duplex-specific nuclease," *Analytical Biochemistry*, Feb. 2012; 421(1):81-85.
Soares et al., "Construction and characterization of a normalized cDNA library," *Proc. Natl. Acad. Sci. USA*, Sep. 1994; 91:9228-9232.
Zhulidov et al., "Simple cDNA normalization using kamchatka crab duplex-specific nuclease," *Nucleic Acids Research*, Jan. 2004; 32(3):e37,1-8.
Boeke et al., "Transcription and reverse transcription of retrotransposons," *Annu Rev Microbiol.*, Oct. 1989; 43:403-34.
Britten et al., "Repeated sequences in DNA. Hundreds of thousands of copies of DNA sequences have been incorporated into the genomes of higher organisms," *Science*, Aug. 1968; 161(3841):529-540.
Brown et al., "Retroviral integration: structure of the initial covalent product and its precursor, and a role for the viral IN protein," *Proc Natl Acad Sci USA*, Apr. 1989; 86(8):2525-9.
Colegio et al., "In vitro transposition system for efficient generation of random mutants of Campylobacter jejuni," *J. Bacteriol.*, Apr. 2001; 183(7): 2384-8.
Craig, "V(D)J recombination and transposition: closer than expected," *Science*, Mar. 1996; 271(5255):1512.

(Continued)

Primary Examiner — Karla A Dines
(74) Attorney, Agent, or Firm — Mueting, Raasch & Gebhardt, P.A.

(57) ABSTRACT

Presented herein are methods and compositions for analyzing rare nucleic acid species. Some methods presented herein use DNA reassociation kinetics following thermal denaturation to define populations of nucleic acid sequences, e.g., highly abundant (e.g., cDNA from rRNA), moderately abundant, and less abundant or rare sequences (e.g., cDNA from mRNA).

19 Claims, 13 Drawing Sheets

Specification includes a Sequence Listing.

(56) References Cited

OTHER PUBLICATIONS

Craig, "Transposon Tn7," *Curr Top Microbiol Immunol.*, 1996; 204:27-48.

Devine et al., "Efficient integration of artificial transposons into plasmid targets in vitro: a useful tool for DNA mapping, sequencing and genetic analysis," *Nucleic Acids Res.*, Sep. 1994; 22(18):3765-72.

Gloor, "Gene targeting in *Drosophila*," *Methods Mol. Biol.*, 2004; 260:97-114.

Goryshin et al., "Tn5 in vitro transposition," *J. Biol. Chem.*, Mar. 1998; 273(13):7367-74.

Ichikawa et al., "In vitro transposition of transposon Tn3," *J Biol. Chem.*, Nov. 1990; 265(31):18829-32.

Kirby et al., "Cryptic plasmids of *Mycobacterium avium*: Tn552 to the rescue," *Mol. Microbiol.*, Jan. 2002; 43(1):173-86.

Kleckner et al., "Tn10 and IS10 transposition and chromosome rearrangements: mechanism and regulation in vivo and in vitro," *Curr Top Microbiol Immunol*, 1996; 204:49-82.

Lampe et al., "A purified mariner transposase is sufficient to mediate transposition in vitro," *EMBO J.*, Oct. 1996; 15(19):5470-9.

Mizuuchi, "In vitro transposition of bacteriophage Mu: a biochemical approach to a novel replication reaction," *Cell*, Dec. 1983; 35(3 Pt 2):785-94.

Ohtsubo et al., "Bacterial insertion sequences," *Curr. Top. Microbiol. Immunol.*, 1996; 204:1-26.

Plasterk, "The Tc1/mariner transposon family," *Curr. Topics Microbiol. Immunol.*, 1996; 204:125-43.

Savilahti et al., "The phage Mu transpososome core: DNA requirements for assembly and function," *EMBO J.*, Oct. 1995; 14(19):4893-4903.

Wilson et al., "New transposon delivery plasmids for insertional mutagenesis in *Bacillus anthracis*," *J. Microbiol. Methods*, Dec. 2007; 71(3):332-5.

Zhang et al., "A Novel Mechanism of Transposon-Mediated Gene Activation," *PLoS Genet.*, Oct. 2009; 5(10):e1000689.

\* cited by examiner

SEQUENCE LISTING

<160> NUMBER OF SEQ ID NOS: 22

<210> SEQ ID NO 1
<211> LENGTH: 476
<212> TYPE: PRT
<213> ORGANISM: Unknown
<220> FEATURE:

<223> OTHER INFORMATION: Transposase Tn5

<400> SEQUENCE: 1

```
Met Ile Thr Ser Ala Leu His Arg Ala Ala Asp Trp Ala Lys Ser Val
 1               5                  10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400
```

```
Glu Cys Gln Leu Leu Gly Tyr Leu Asp Lys Gly Lys Arg Lys Lys
                    405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 2
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 2

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Trp Val His Ser
            115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Xaa Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270
```

```
Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
                355                 360                 365

Ser Phe Thr Leu Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
                435                 440                 445

Leu Trp Glu Gly Trp Glu Ala Leu Gln Ser Lys Leu Asp Gly Phe Leu
            450                 455                 460

Ala Ala Lys Asp Leu Met Ala Gln Gly Ile Lys Ile
465                 470                 475

<210> SEQ ID NO 3
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V

<400> SEQUENCE: 3

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
                35                  40                  45

Ser Ser Glu Gly Ser Glu Ala Met Gln Glu Gly Ala Tyr Arg Phe Ile
            50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Xaa Lys Ser Arg Gly Trp Trp Val His Ser
            115                 120                 125

Val Leu Leu Leu Glu Ala Thr Thr Phe Arg Thr Val Gly Leu Leu His
```

130                 135                 140
Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
            165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
            210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
            290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
            325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
            450                 455                 460

Ala Ala Lys Asp Leu Met Ala Gln Gly Ile Lys Ile
465                 470                 475

<210> SEQ ID NO 4
<211> LENGTH: 476
<212> TYPE: PRT
<213> ORGANISM: Unknown
<220> FEATURE:
<223> OTHER INFORMATION: Transposase Tn5

<400> SEQUENCE: 4

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val

-continued

```
                20                  25                  30
Asn Val Ala Ala Gln Leu Ala Lys Tyr Ser Gly Lys Ser Ile Thr Ile
         35                  40                  45
Ser Ser Glu Gly Ser Glu Ala Met Gln Glu Gly Ala Tyr Arg Phe Ile
     50                  55                  60
Arg Asn Pro Asn Val Ser Ala Glu Ala Ile Arg Lys Ala Gly Ala Met
 65                  70                  75                  80
Gln Thr Val Lys Leu Ala Gln Glu Phe Pro Glu Leu Leu Ala Ile Glu
                 85                  90                  95
Asp Thr Thr Ser Leu Ser Tyr Arg His Gln Val Ala Glu Glu Leu Gly
             100                 105                 110
Lys Leu Gly Ser Ile Gln Asp Lys Ser Arg Gly Trp Met Val His Ser
         115                 120                 125
Val Leu Leu Leu Glu Ala Thr Thr Phe Arg Thr Val Gly Leu Leu His
     130                 135                 140
Gln Glu Trp Trp Met Arg Pro Asp Asp Pro Ala Asp Ala Asp Glu Lys
145                 150                 155                 160
Glu Ser Gly Lys Trp Leu Ala Ala Ala Thr Ser Arg Leu Arg Met
                 165                 170                 175
Gly Ser Met Met Ser Asn Val Ile Ala Val Cys Asp Arg Glu Ala Asp
             180                 185                 190
Ile His Ala Tyr Leu Gln Asp Lys Leu Ala His Asn Glu Arg Phe Val
         195                 200                 205
Val Arg Ser Lys His Pro Arg Lys Asp Val Glu Ser Gly Leu Tyr Leu
     210                 215                 220
Tyr Asp His Leu Lys Asn Gln Pro Glu Leu Gly Gly Tyr Gln Ile Ser
225                 230                 235                 240
Ile Pro Gln Lys Gly Val Val Asp Lys Arg Gly Lys Arg Lys Asn Arg
                 245                 250                 255
Pro Ala Arg Lys Ala Ser Leu Ser Leu Arg Ser Gly Arg Ile Thr Leu
             260                 265                 270
Lys Gln Gly Asn Ile Thr Leu Asn Ala Val Leu Ala Glu Glu Ile Asn
         275                 280                 285
Pro Pro Lys Gly Glu Thr Pro Leu Lys Trp Leu Leu Leu Thr Ser Glu
     290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                 325                 330                 335
Gly Ala Glu Arg Gln Arg Met Glu Glu Pro Asp Asn Leu Glu Arg Met
             340                 345                 350
Val Ser Ile Leu Ser Phe Val Ala Val Arg Leu Leu Gln Leu Arg Glu
         355                 360                 365
Ser Phe Thr Leu Pro Gln Ala Leu Arg Ala Gln Gly Leu Leu Lys Glu
     370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                 405                 410                 415
Glu Lys Ala Gly Ser Leu Gln Trp Ala Tyr Met Ala Ile Ala Arg Leu
             420                 425                 430
Gly Gly Phe Met Asp Ser Lys Arg Thr Gly Ile Ala Ser Trp Gly Ala
         435                 440                 445
```

```
Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 5
<211> LENGTH: 477
<212> TYPE: PRT
<213> ORGANISM: Unknown
<220> FEATURE:
<223> OTHER INFORMATION: Transposase Tn5

<400> SEQUENCE: 5

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Val Lys Arg Gly Lys Arg Lys Asn
                245                 250                 255

Arg Pro Ala Arg Lys Ala Ser Leu Ser Leu Arg Ser Gly Arg Ile Thr
            260                 265                 270

Leu Lys Gln Gly Asn Ile Thr Leu Asn Ala Val Leu Ala Glu Glu Ile
        275                 280                 285

Asn Pro Pro Lys Gly Glu Thr Pro Leu Lys Trp Leu Leu Leu Thr Ser
    290                 295                 300

Glu Pro Val Glu Ser Leu Ala Gln Ala Leu Arg Val Ile Asp Ile Tyr
305                 310                 315                 320

Thr His Arg Trp Arg Ile Glu Glu Phe His Lys Ala Trp Lys Thr Gly
                325                 330                 335
```

-continued

```
Ala Gly Ala Glu Arg Gln Arg Met Glu Glu Pro Asp Asn Leu Glu Arg
            340                 345                 350

Met Val Ser Ile Leu Ser Phe Val Ala Val Arg Leu Leu Gln Leu Arg
            355                 360                 365

Glu Ser Phe Thr Leu Pro Gln Ala Leu Arg Ala Gln Gly Leu Leu Lys
            370                 375                 380

Glu Ala Glu His Val Glu Ser Gln Ser Ala Glu Thr Val Leu Thr Pro
385                 390                 395                 400

Asp Glu Cys Gln Leu Leu Gly Tyr Leu Asp Lys Gly Lys Arg Lys Arg
                405                 410                 415

Lys Glu Lys Ala Gly Ser Leu Gln Trp Ala Tyr Met Ala Ile Ala Arg
            420                 425                 430

Leu Gly Gly Phe Met Asp Ser Lys Arg Thr Gly Ile Ala Ser Trp Gly
            435                 440                 445

Ala Leu Trp Glu Gly Trp Glu Ala Leu Gln Ser Lys Leu Asp Gly Phe
            450                 455                 460

Leu Ala Ala Lys Asp Leu Met Ala Gln Gly Ile Lys Ile
465                 470                 475
```

<210> SEQ ID NO 6
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (120)..(120)
<223> OTHER INFORMATION: X = Y, F, W, E

<400> SEQUENCE: 6

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
            85                  90                  95

Asp Thr Thr Ser Leu Ser Tyr Arg His Gln Val Ala Glu Glu Leu Gly
            100                 105                 110

Lys Leu Gly Ser Ile Gln Asp Xaa Ser Arg Gly Trp Trp Val His Ser
            115                 120                 125

Val Leu Leu Leu Glu Ala Thr Thr Phe Arg Thr Val Gly Leu Leu His
            130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
```

```
                195                 200                 205
Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Asp Lys Gly Lys Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
                275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
                355                 360                 365

Ser Phe Thr Leu Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
                435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475
```

<210> SEQ ID NO 7
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V
<220> FEATURE:
<221> NAME/KEY: Variant
<222> LOCATION: (120)..(120)
<223> OTHER INFORMATION: X = Y, F, W, E
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 7

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
```

```
                    20                  25                  30
Asn Val Ala Ala Gln Leu Ala Lys Tyr Ser Gly Lys Ser Ile Thr Ile
                35                  40                  45
Ser Ser Glu Gly Ser Glu Ala Met Gln Glu Gly Ala Tyr Arg Phe Ile
            50                  55                  60
Arg Asn Pro Asn Val Ser Ala Glu Ala Ile Arg Lys Ala Gly Ala Met
 65                  70                  75                  80
Gln Thr Val Lys Leu Ala Gln Glu Phe Pro Glu Leu Leu Ala Ile Glu
                85                  90                  95
Asp Thr Thr Ser Leu Ser Tyr Arg His Gln Val Ala Glu Glu Leu Gly
                100                 105                 110
Lys Leu Gly Ser Ile Gln Xaa Xaa Ser Arg Gly Trp Met Val His Ser
                115                 120                 125
Val Leu Leu Leu Glu Ala Thr Thr Phe Arg Thr Val Gly Leu Leu His
                130                 135                 140
Gln Glu Trp Trp Met Arg Pro Asp Asp Pro Ala Asp Ala Asp Glu Lys
145                 150                 155                 160
Glu Ser Gly Lys Trp Leu Ala Ala Ala Thr Ser Arg Leu Arg Met
                165                 170                 175
Gly Ser Met Met Ser Asn Val Ile Ala Val Cys Asp Arg Glu Ala Asp
                180                 185                 190
Ile His Ala Tyr Leu Gln Asp Lys Leu Ala His Asn Glu Arg Phe Val
                195                 200                 205
Val Arg Ser Lys His Pro Arg Lys Asp Val Glu Ser Gly Leu Tyr Leu
                210                 215                 220
Tyr Asp His Leu Lys Asn Gln Pro Glu Leu Gly Gly Tyr Gln Ile Ser
225                 230                 235                 240
Ile Pro Gln Lys Gly Val Val Xaa Lys Arg Gly Lys Arg Lys Asn Arg
                245                 250                 255
Pro Ala Arg Lys Ala Ser Leu Ser Leu Arg Ser Gly Arg Ile Thr Leu
                260                 265                 270
Lys Gln Gly Asn Ile Thr Leu Asn Ala Val Leu Ala Glu Glu Ile Asn
                275                 280                 285
Pro Pro Lys Gly Glu Thr Pro Leu Lys Trp Leu Leu Leu Thr Ser Glu
                290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Glu Pro Asp Asn Leu Glu Arg Met
                340                 345                 350
Val Ser Ile Leu Ser Phe Val Ala Val Arg Leu Leu Gln Leu Arg Glu
                355                 360                 365
Ser Phe Thr Leu Pro Gln Ala Leu Arg Ala Gln Gly Leu Leu Lys Glu
                370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
                420                 425                 430
Gly Gly Phe Met Asp Ser Lys Arg Thr Gly Ile Ala Ser Trp Gly Ala
                435                 440                 445
```

-continued

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 8
<211> LENGTH: 476
<212> TYPE: PRT
<213> ORGANISM: Unknown
<220> FEATURE:
<223> OTHER INFORMATION: Transposase Tn5

<400> SEQUENCE: 8

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

```
Gly Val Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475
```

<210> SEQ ID NO 9
<211> LENGTH: 476
<212> TYPE: PRT
<213> ORGANISM: Unknown
<220> FEATURE:
<223> OTHER INFORMATION: Transposase Tn5

<400> SEQUENCE: 9

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
    210                 215                 220
```

Tyr Asp His Leu Lys Asn Gln Pro Glu Leu Gly Gly Tyr Gln Ile Ser
225                 230                 235                 240

Ile Pro Gln Lys Gly Val Asp Lys Arg Lys Arg Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
            325                 330                 335

Gly Val Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
            405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
            450                 455                 460

Ala Ala Lys Asp Leu Met Ala Gln Gly Ile Lys Ile
465                 470                 475

<210> SEQ ID NO 10
<211> LENGTH: 476
<212> TYPE: PRT
<213> ORGANISM: Unknown
<220> FEATURE:
<223> OTHER INFORMATION: Transposase Tn5

<400> SEQUENCE: 10

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
            50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
            85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
            115                 120                 125

Val Leu Leu Glu Ala Thr Thr Phe Arg Thr Val Gly Leu Leu His
    130                 135                 140

Gln Gln Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Gly Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 11
<211> LENGTH: 476
<212> TYPE: PRT
<213> ORGANISM: Unknown
<220> FEATURE:
<223> OTHER INFORMATION: Transposase Tn5

<400> SEQUENCE: 11

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415
```

-continued

```
Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
450                 455                 460

Ala Ala Lys Asp Leu Met Ala Gln Gly Ile Lys Ile
465                 470                 475

<210> SEQ ID NO 12
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: VARIANT
<222> LOCATION: (248)..(248)
<223> OTHER INFORMATION: X = Y, T, K, S, L, A, W, P, G, R, F, H

<400> SEQUENCE: 12

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Xaa Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285
```

-continued

```
Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Pro Asp Asn Leu Glu Arg Met
                340                 345                 350

Val Ser Ile Leu Ser Phe Val Ala Val Arg Leu Leu Gln Leu Arg Glu
                355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 13
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V

<400> SEQUENCE: 13

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Xaa Lys Ser Arg Gly Trp Trp Val His Ser
    115                 120                 125

Val Leu Leu Leu Glu Ala Thr Thr Phe Arg Thr Val Gly Leu Leu His
        130                 135                 140

Gln Glu Trp Trp Met Arg Pro Asp Asp Pro Ala Asp Ala Asp Glu Lys
```

|     |     |     |     | 145 |     |     |     | 150 |     |     |     | 155 |     |     |     | 160 |
| --- | --- | --- | --- | --- | --- | --- | --- | --- | --- | --- | --- | --- | --- | --- | --- | --- |

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 14
<211> LENGTH: 476
<212> TYPE: PRT
<213> ORGANISM: Unknown
<220> FEATURE:
<223> OTHER INFORMATION: Transposase Tn5

<400> SEQUENCE: 14

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile

```
              35                  40                  45
Ser Ser Glu Gly Ser Lys Ala Ala Gln Glu Gly Ala Tyr Arg Phe Ile
 50                  55                  60

Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
                 85                  90                  95

Asp Thr Thr Ser Leu Ser Tyr Arg His Gln Val Ala Glu Glu Leu Gly
                100                 105                 110

Lys Leu Gly Ser Ile Gln Asp Lys Ser Arg Gly Trp Met Val His Ser
                115                 120                 125

Val Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
            355                 360                 365

Ser Phe Thr Pro Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
450                 455                 460
```

```
Ala Ala Lys Asp Leu Met Ala Gln Gly Ile Lys Ile
465                 470                 475
```

<210> SEQ ID NO 15
<211> LENGTH: 477
<212> TYPE: PRT
<213> ORGANISM: Unknown
<220> FEATURE:
<223> OTHER INFORMATION: Transposase Tn5

<400> SEQUENCE: 15

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Val Lys Arg Gly Lys Arg Lys Asn
                245                 250                 255

Arg Pro Ala Arg Lys Ala Ser Leu Ser Leu Arg Ser Gly Arg Ile Thr
            260                 265                 270

Leu Lys Gln Gly Asn Ile Thr Leu Asn Ala Val Leu Ala Glu Glu Ile
        275                 280                 285

Asn Pro Pro Lys Gly Glu Thr Pro Leu Lys Trp Leu Leu Leu Thr Ser
290                 295                 300

Glu Pro Val Glu Ser Leu Ala Gln Ala Leu Arg Val Ile Asp Ile Tyr
305                 310                 315                 320

Thr His Arg Trp Arg Ile Glu Glu Phe His Lys Ala Trp Lys Thr Gly
                325                 330                 335

Ala Gly Ala Glu Arg Gln Arg Met Glu Glu Pro Asp Asn Leu Glu Arg
            340                 345                 350
```

```
Met Val Ser Ile Leu Ser Phe Val Ala Val Arg Leu Leu Gln Leu Arg
            355                 360                 365

Glu Ser Phe Thr Pro Pro Gln Ala Leu Arg Ala Gln Gly Leu Leu Lys
        370                 375                 380

Glu Ala Glu His Val Glu Ser Gln Ser Ala Glu Thr Val Leu Thr Pro
385                 390                 395                 400

Asp Glu Cys Gln Leu Leu Gly Tyr Leu Asp Lys Gly Lys Arg Lys Arg
                405                 410                 415

Lys Glu Lys Ala Gly Ser Leu Gln Trp Ala Tyr Met Ala Ile Ala Arg
                420                 425                 430

Leu Gly Gly Phe Met Asp Ser Lys Arg Thr Gly Ile Ala Ser Trp Gly
            435                 440                 445

Ala Leu Trp Glu Gly Trp Glu Ala Leu Gln Ser Lys Leu Asp Gly Phe
        450                 455                 460

Leu Ala Ala Lys Asp Leu Met Ala Gln Gly Ile Lys Ile
465                 470                 475

<210> SEQ ID NO 16
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (120)..(120)
<223> OTHER INFORMATION: X = Y, F, W, E

<400> SEQUENCE: 16

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
                100                 105                 110

Lys Leu Gly Ser Ile Gln Asp Xaa Ser Arg Gly Trp Trp Val His Ser
            115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
```

```
            210                 215                 220
Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Gly Pro Asp Asn Leu Glu Arg Met
            340                 345                 350

Val Ser Ile Leu Ser Phe Val Ala Val Arg Leu Leu Gln Leu Arg Glu
                355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
                435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 17
<211> LENGTH: 476
<212> TYPE: PRT
<213> ORGANISM: Unknown
<220> FEATURE:
<223> OTHER INFORMATION: Transposase Tn5
<220> FEATURE:
<221> NAME/KEY: Variant
<222> LOCATION: (119)..(119)
<223> OTHER INFORMATION: X = L, M, S, A, V
<220> FEATURE:
<221> NAME/KEY: Variant
<222> LOCATION: (120)..(120)
<223> OTHER INFORMATION: X = Y, F, W, E
<220> FEATURE:
<221> NAME/KEY: Variant
<222> LOCATION: (248)..(248)
<223> OTHER INFORMATION: X = Y, T, K, S, L, A, W, P, G, R, F, H

<400> SEQUENCE: 17

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
```

```
                    35                  40                  45
Ser Ser Glu Gly Ser Lys Ala Ala Gln Glu Gly Ala Tyr Arg Phe Ile
 50                  55                  60

Arg Asn Pro Asn Val Ser Ala Glu Ala Ile Arg Lys Ala Gly Ala Met
 65                  70                  75                  80

Gln Thr Val Lys Leu Ala Gln Glu Phe Pro Glu Leu Leu Ala Ile Glu
                 85                  90                  95

Asp Thr Thr Ser Leu Ser Tyr Arg His Gln Val Ala Glu Glu Leu Gly
                100                 105                 110

Lys Leu Gly Ser Ile Gln Xaa Xaa Ser Arg Gly Trp Met Val His Ser
            115                 120                 125

Val Leu Leu Glu Ala Thr Thr Phe Arg Thr Val Gly Leu Leu His
        130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
                180                 185                 190

Ile His Ala Tyr Leu Gln Asp Lys Leu Ala His Asn Glu Arg Phe Val
            195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Xaa Lys Arg Gly Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
                340                 345                 350

Val Ser Ile Leu Ser Phe Val Ala Val Arg Leu Leu Gln Leu Arg Glu
            355                 360                 365

Ser Phe Thr Pro Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
450                 455                 460
```

Ala Ala Lys Asp Leu Met Ala Gln Gly Ile Lys Ile
465                 470                 475

<210> SEQ ID NO 18
<211> LENGTH: 476
<212> TYPE: PRT
<213> ORGANISM: Unknown
<220> FEATURE:
<223> OTHER INFORMATION: Transposase Tn5

<400> SEQUENCE: 18

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Val Glu Arg Gln Arg Met Glu Glu Pro Asp Asn Leu Glu Arg Met
            340                 345                 350

```
Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
        450                 455                 460

Ala Ala Lys Asp Leu Met Ala Gln Gly Ile Lys Ile
465                 470                 475

<210> SEQ ID NO 19
<211> LENGTH: 476
<212> TYPE: PRT
<213> ORGANISM: Unknown
<220> FEATURE:
<223> OTHER INFORMATION: Transposase Tn5

<400> SEQUENCE: 19

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Arg His Arg Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240
```

```
Ile Pro Gln Lys Gly Val Val Asp Lys Arg Arg Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Val Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 20
<211> LENGTH: 476
<212> TYPE: PRT
<213> ORGANISM: Unknown
<220> FEATURE:
<223> OTHER INFORMATION: Transposase Tn5

<400> SEQUENCE: 20

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Lys Ala Ala Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125
```

```
Val Leu Leu Leu Glu Ala Thr Thr Phe Arg Thr Val Gly Leu Leu His
        130                 135                 140

Gln Gln Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Gly Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Arg Lys Arg Lys Asn Arg
                245                 250                 255

Pro Ala Arg Lys Ala Ser Leu Ser Leu Arg Ser Gly Arg Ile Thr Leu
                260                 265                 270

Lys Gln Gly Asn Ile Thr Leu Asn Ala Val Leu Ala Glu Glu Ile Asn
            275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Pro Pro Gln Ala Leu Arg Ala Gln Gly Leu Leu Lys Glu
        370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
                420                 425                 430

Gly Gly Phe Met Asp Ser Lys Arg Thr Gly Ile Ala Ser Trp Gly Ala
            435                 440                 445

Leu Trp Glu Gly Trp Ala Leu Gln Ser Lys Leu Asp Gly Phe Leu
        450                 455                 460

Ala Ala Lys Asp Leu Met Ala Gln Gly Ile Lys Ile
465                 470                 475

<210> SEQ ID NO 21
<211> LENGTH: 760
<212> TYPE: PRT
<213> ORGANISM: Unknown
<220> FEATURE:
<223> OTHER INFORMATION: TS-Tn5 Fusion Protein Amino Acid Sequence

<400> SEQUENCE: 21

Met Ala Glu Ile Thr Ala Ser Leu Val Lys Glu Leu Arg Glu Arg Thr
1               5                   10                  15
```

```
Gly Ala Gly Met Met Asp Cys Lys Lys Ala Leu Thr Glu Ala Asn Gly
            20                  25                  30

Asp Ile Glu Leu Ala Ile Glu Asn Met Arg Lys Ser Gly Ala Ile Lys
        35                  40                  45

Ala Ala Lys Lys Ala Gly Asn Val Ala Ala Asp Gly Val Ile Lys Thr
50                  55                  60

Lys Ile Asp Gly Asn Tyr Gly Ile Ile Leu Glu Val Asn Cys Gln Thr
65                  70                  75                  80

Asp Phe Val Ala Lys Asp Ala Gly Phe Gln Ala Phe Ala Asp Lys Val
                85                  90                  95

Leu Asp Ala Ala Val Ala Gly Lys Ile Thr Asp Val Glu Val Leu Lys
                100                 105                 110

Ala Gln Phe Glu Glu Glu Arg Val Ala Leu Val Ala Lys Ile Gly Glu
        115                 120                 125

Asn Ile Asn Ile Arg Arg Val Ala Ala Leu Glu Gly Asp Val Leu Gly
130                 135                 140

Ser Tyr Gln His Gly Ala Arg Ile Gly Val Leu Val Ala Ala Lys Gly
145                 150                 155                 160

Ala Asp Glu Glu Leu Val Lys His Ile Ala Met His Val Ala Ala Ser
                165                 170                 175

Lys Pro Glu Phe Ile Lys Pro Glu Asp Val Ser Ala Glu Val Val Glu
                180                 185                 190

Lys Glu Tyr Gln Val Gln Leu Asp Ile Ala Met Gln Ser Gly Lys Pro
        195                 200                 205

Lys Glu Ile Ala Glu Lys Met Val Glu Gly Arg Met Lys Lys Phe Thr
210                 215                 220

Gly Glu Val Ser Leu Thr Gly Gln Pro Phe Val Met Glu Pro Ser Lys
225                 230                 235                 240

Thr Val Gly Gln Leu Leu Lys Glu His Asn Ala Glu Val Thr Gly Phe
                245                 250                 255

Ile Arg Phe Glu Val Gly Gly Ile Glu Lys Val Glu Thr Asp Phe
                260                 265                 270

Ala Ala Glu Val Ala Ala Met Ser Lys Gln Ser Gly Thr Ile Thr Ser
        275                 280                 285

Ala Leu His Arg Ala Ala Asp Trp Ala Lys Ser Val Phe Ser Ser Ala
290                 295                 300

Ala Leu Gly Asp Pro Arg Arg Thr Ala Arg Leu Val Asn Val Ala Ala
305                 310                 315                 320

Gln Leu Ala Lys Tyr Ser Gly Lys Ser Ile Thr Ile Ser Ser Glu Gly
                325                 330                 335

Ser Lys Ala Ala Gln Glu Gly Ala Tyr Arg Phe Ile Arg Asn Pro Asn
                340                 345                 350

Val Ser Ala Glu Ala Ile Arg Lys Ala Gly Ala Met Gln Thr Val Lys
        355                 360                 365

Leu Ala Gln Glu Phe Pro Glu Leu Leu Ala Ile Glu Asp Thr Thr Ser
370                 375                 380

Leu Ser Tyr Arg His Gln Val Ala Glu Glu Leu Gly Lys Leu Gly Ser
385                 390                 395                 400

Ile Gln Asp Lys Ser Arg Gly Trp Trp Val His Ser Val Leu Leu Leu
                405                 410                 415

Glu Ala Thr Thr Phe Arg Thr Val Gly Leu Leu His Gln Glu Trp Trp
                420                 425                 430
```

```
Met Arg Pro Asp Asp Pro Ala Asp Ala Asp Glu Lys Glu Ser Gly Lys
            435                 440                 445

Trp Leu Ala Ala Ala Thr Ser Arg Leu Arg Met Gly Ser Met Met
    450                 455                 460

Ser Asn Val Ile Ala Val Cys Asp Arg Glu Ala Asp Ile His Ala Tyr
465                 470                 475                 480

Leu Gln Asp Lys Leu Ala His Asn Glu Arg Phe Val Val Arg Ser Lys
                485                 490                 495

His Pro Arg Lys Asp Val Glu Ser Gly Leu Tyr Leu Tyr Asp His Leu
            500                 505                 510

Lys Asn Gln Pro Glu Leu Gly Gly Tyr Gln Ile Ser Ile Pro Gln Lys
        515                 520                 525

Gly Val Val Asp Lys Arg Gly Lys Arg Lys Asn Arg Pro Ala Arg Lys
    530                 535                 540

Ala Ser Leu Ser Leu Arg Ser Gly Arg Ile Thr Leu Lys Gln Gly Asn
545                 550                 555                 560

Ile Thr Leu Asn Ala Val Leu Ala Glu Glu Ile Asn Pro Pro Lys Gly
                565                 570                 575

Glu Thr Pro Leu Lys Trp Leu Leu Leu Thr Ser Glu Pro Val Glu Ser
            580                 585                 590

Leu Ala Gln Ala Leu Arg Val Ile Asp Ile Tyr Thr His Arg Trp Arg
        595                 600                 605

Ile Glu Glu Phe His Lys Ala Trp Lys Thr Gly Ala Gly Ala Glu Arg
    610                 615                 620

Gln Arg Met Glu Glu Pro Asp Asn Leu Glu Arg Met Val Ser Ile Leu
625                 630                 635                 640

Ser Phe Val Ala Val Arg Leu Leu Gln Leu Arg Glu Ser Phe Thr Pro
                645                 650                 655

Pro Gln Ala Leu Arg Ala Gln Gly Leu Leu Lys Glu Ala Glu His Val
            660                 665                 670

Glu Ser Gln Ser Ala Glu Thr Val Leu Thr Pro Asp Glu Cys Gln Leu
        675                 680                 685

Leu Gly Tyr Leu Asp Lys Gly Lys Arg Lys Arg Lys Glu Lys Ala Gly
    690                 695                 700

Ser Leu Gln Trp Ala Tyr Met Ala Ile Ala Arg Leu Gly Gly Phe Met
705                 710                 715                 720

Asp Ser Lys Arg Thr Gly Ile Ala Ser Trp Gly Ala Leu Trp Glu Gly
                725                 730                 735

Trp Glu Ala Leu Gln Ser Lys Leu Asp Gly Phe Leu Ala Ala Lys Asp
            740                 745                 750

Leu Met Ala Gln Gly Ile Lys Ile
        755                 760

<210> SEQ ID NO 22
<211> LENGTH: 760
<212> TYPE: PRT
<213> ORGANISM: unknown
<220> FEATURE:
<223> OTHER INFORMATION: TS-Tn mutant protein

<400> SEQUENCE: 22

Met Ala Glu Ile Thr Ala Ser Leu Val Lys Glu Leu Arg Glu Arg Thr
1               5                   10                  15

Gly Ala Gly Met Met Asp Cys Lys Lys Ala Leu Thr Glu Ala Asn Gly
            20                  25                  30
```

-continued

```
Asp Ile Glu Leu Ala Ile Glu Asn Met Arg Lys Ser Gly Ala Ile Lys
 35                  40                  45
Ala Ala Lys Lys Ala Gly Asn Val Ala Ala Asp Gly Val Ile Lys Thr
 50                  55                  60
Lys Ile Asp Gly Asn Tyr Gly Ile Ile Leu Glu Val Asn Cys Gln Thr
65                   70                  75                  80
Asp Phe Val Ala Lys Asp Ala Gly Phe Gln Ala Phe Ala Asp Lys Val
                 85                  90                  95
Leu Asp Ala Ala Val Ala Gly Lys Ile Thr Asp Val Glu Val Leu Lys
                100                 105                 110
Ala Gln Phe Glu Glu Arg Val Ala Leu Val Ala Lys Ile Gly Glu
            115                 120                 125
Asn Ile Asn Ile Arg Arg Val Ala Ala Leu Glu Gly Asp Val Leu Gly
130                 135                 140
Ser Tyr Gln His Gly Ala Arg Ile Gly Val Leu Val Ala Ala Lys Gly
145                 150                 155                 160
Ala Asp Glu Glu Leu Val Lys His Ile Ala Met His Val Ala Ala Ser
                165                 170                 175
Lys Pro Glu Phe Ile Lys Pro Glu Asp Val Ser Ala Glu Val Val Glu
                180                 185                 190
Lys Glu Tyr Gln Val Gln Leu Asp Ile Ala Met Gln Ser Gly Lys Pro
            195                 200                 205
Lys Glu Ile Ala Glu Lys Met Val Glu Gly Arg Met Lys Lys Phe Thr
210                 215                 220
Gly Glu Val Ser Leu Thr Gly Gln Pro Phe Val Met Glu Pro Ser Lys
225                 230                 235                 240
Thr Val Gly Gln Leu Leu Lys Glu His Asn Ala Glu Val Thr Gly Phe
                245                 250                 255
Ile Arg Phe Glu Val Gly Glu Gly Ile Glu Lys Val Glu Thr Asp Phe
                260                 265                 270
Ala Ala Glu Val Ala Ala Met Ser Lys Gln Ser Gly Thr Ile Thr Ser
            275                 280                 285
Ala Leu His Arg Ala Ala Asp Trp Ala Lys Ser Val Phe Ser Ser Ala
290                 295                 300
Ala Leu Gly Asp Pro Arg Arg Thr Ala Arg Leu Val Asn Val Ala Ala
305                 310                 315                 320
Gln Leu Ala Lys Tyr Ser Gly Lys Ser Ile Thr Ile Ser Ser Glu Gly
                325                 330                 335
Ser Lys Ala Ala Gln Glu Gly Ala Tyr Arg Phe Ile Arg Asn Pro Asn
                340                 345                 350
Val Ser Ala Glu Ala Ile Arg Lys Ala Gly Ala Met Gln Thr Val Lys
            355                 360                 365
Leu Ala Gln Glu Phe Pro Glu Leu Leu Ala Ile Glu Asp Thr Thr Ser
370                 375                 380
Leu Ser Tyr Arg His Gln Val Ala Glu Glu Leu Gly Lys Leu Gly Ser
385                 390                 395                 400
Ile Gln Asp Lys Ser Arg Gly Trp Trp Val His Ser Val Leu Leu Leu
                405                 410                 415
Glu Ala Thr Thr Phe Arg Thr Val Gly Leu Leu His Gln Glu Trp Trp
                420                 425                 430
Met Arg Pro Asp Asp Pro Ala Asp Ala Asp Glu Lys Glu Ser Gly Lys
            435                 440                 445
Trp Leu Ala Ala Ala Ala Thr Ser Arg Leu Arg Met Gly Ser Met Met
```

```
                450             455             460
Ser Asn Val Ile Ala Val Cys Asp Arg Glu Ala Asp Ile His Ala Tyr
465                 470                 475                 480

Leu Gln Asp Lys Leu Ala His Asn Glu Arg Phe Val Val Arg Ser Arg
                485                 490                 495

His Arg Arg Lys Asp Val Glu Ser Gly Leu Tyr Leu Tyr Asp His Leu
                500                 505                 510

Lys Asn Gln Pro Glu Leu Gly Gly Tyr Gln Ile Ser Ile Pro Gln Lys
                515                 520                 525

Gly Val Val Asp Lys Arg Arg Lys Arg Lys Asn Arg Pro Ala Arg Lys
                530                 535                 540

Ala Ser Leu Ser Leu Arg Ser Gly Arg Ile Thr Leu Lys Gln Gly Asn
545                 550                 555                 560

Ile Thr Leu Asn Ala Val Leu Ala Glu Glu Ile Asn Pro Pro Lys Gly
                565                 570                 575

Glu Thr Pro Leu Lys Trp Leu Leu Leu Thr Ser Glu Pro Val Glu Ser
                580                 585                 590

Leu Ala Gln Ala Leu Arg Val Ile Asp Ile Tyr Thr His Arg Trp Arg
                595                 600                 605

Ile Glu Glu Phe His Lys Ala Trp Lys Thr Gly Ala Gly Val Glu Arg
                610                 615                 620

Gln Arg Met Glu Glu Pro Asp Asn Leu Glu Arg Met Val Ser Ile Leu
625                 630                 635                 640

Ser Phe Val Ala Val Arg Leu Leu Gln Leu Arg Glu Ser Phe Thr Pro
                645                 650                 655

Pro Gln Ala Leu Arg Ala Gln Gly Leu Leu Lys Glu Ala Glu His Val
                660                 665                 670

Glu Ser Gln Ser Ala Glu Thr Val Leu Thr Pro Asp Glu Cys Gln Leu
                675                 680                 685

Leu Gly Tyr Leu Asp Lys Gly Lys Arg Lys Arg Lys Glu Lys Ala Gly
                690                 695                 700

Ser Leu Gln Trp Ala Tyr Met Ala Ile Ala Arg Leu Gly Gly Phe Met
705                 710                 715                 720

Asp Ser Lys Arg Thr Gly Ile Ala Ser Trp Gly Ala Leu Trp Glu Gly
                725                 730                 735

Trp Glu Ala Leu Gln Ser Lys Leu Asp Gly Phe Leu Ala Ala Lys Asp
                740                 745                 750

Leu Met Ala Gln Gly Ile Lys Ile
                755                 760
```

METHODS OF ANALYZING NUCLEIC ACIDS

This application is the § 371 U.S. National Stage of International Application No. PCT/US2016/034809, filed 27 May 2016, which claims the benefit of U.S. Provisional Application No. 62/168,281, filed 29 May 2015, the disclosures of which are incorporated by reference herein in their entireties.

1 BACKGROUND

Current high throughput library preparation methods to analyze genomes and transcriptomes contain sequence information that mostly preserves the natural abundance of genes and transcripts. Typically, genomic libraries from higher eukaryotes, especially plants, contain a significant amount of repetitive DNA. Similarly, transcriptome libraries from both eukaryotes and prokaryotes largely contain cDNA sequences that are derived from a small number of abundant transcripts. Sequence information derived from ribosomal RNA (rRNA) predominate transcriptome libraries even after their removal prior to conversion to cDNA. Further, preparations of nucleic acids from eukaryotes, unless they are fractionated, contain sequences from organelles such as mitochondria and/or chloroplasts and these sequences further constitute a source of unwanted data. While useful for copy number analysis and expression profiling, the complexity of sequence information in these libraries may be a hindrance in the analysis of sequence variants and may mask information derived from low copy genes and transcripts. Therefore, there is a need for methods to reduce the complexity of libraries to aid, for example, in the discovery and analysis of low copy genes, their variants and expressed transcripts.

2 BRIEF SUMMARY

In one aspect, the methods of the invention use DNA reassociation kinetics following thermal denaturation to define populations of nucleic acid sequences, e.g., highly abundant (e.g., cDNA from rRNA), moderately abundant, and less abundant or rare sequences (e.g., cDNA from mRNA). The rate at which a particular sequence will reassociate is proportional to the number of copies of that sequence in the DNA sample. For example, highly-repetitive (abundant) sequence will reassociate rapidly, while complex sequences (less abundant) will reassociate more slowly and remain single-stranded for a longer period of time.

In one embodiment, the methods of the invention provide for selective identification and sequence analysis of both the abundant and less abundant (e.g., rare) species of nucleic acids present in a sample. In some embodiments, a biotinylated transposome is used to selectively tag and capture the more abundant DNA molecules in a DNA library thereby reducing the complexity of abundant sequences in the DNA library. The less abundant DNA molecules remain in the supernatant and may be readily processed for sequence analysis. The tagged and captured abundant DNA molecules may also be readily processed for subsequent analysis.

In another embodiment, the disclosed methods use transposome-based normalization to reduce the impact of abundant sequences (e.g., rRNA) in library sequence analysis.

In one aspect, certain nucleic acids can be selectively captured from a mixture of other nucleic acids and other cellular components. In some embodiments, the nucleic acids that are selectively captured are purified from a mixture of nucleic acids and other cellular components. In some embodiments, certain nucleic acids are selectively purified from a mixture of nucleic acids and other cellular components by removing one or more type of other nucleic acids. In some embodiments, more than one type of nucleic acid can be selectively captured and/or purified from a mixture of nucleic acids or from a biological sample.

In one aspect, the application discloses kits comprising nucleic acid binding proteins immobilized on a solid support to selectively capture and/or purify specific types of nucleic acids from a mixture of various types of nucleic acids. In some embodiments, the kits can be used to purify specific types of nucleic acids bound to the immobilized nucleic acid binding protein. In some embodiments, the kits can be used to enrich unbound nucleic acid in a mixture of nucleic acids.

In some embodiments presented herein is provided a method of analyzing rare nucleic acid species comprising: (a) providing library of double-stranded nucleic acids; (b) denaturing the library; (c) renaturing the library under conditions sufficient to renature abundant nucleic acid species, wherein a portion of the library comprising less abundant nucleic acid species does not renature; (d) contacting the library with a nucleic acid binding protein that preferentially binds to double-stranded nucleic acids; and (e) separating renatured abundant nucleic acid species from the less abundant nucleic acid species.

In certain aspects, separating comprises immobilizing binding protein to a solid support. In certain aspects, said binding protein comprises a transposase. In certain aspects, said binding protein comprises Tn5 or TS-Tn5 transposase. In certain aspects, said binding protein comprises adaptor sequences which comprise a binding moiety capable of binding to a solid support. In certain aspects, said binding protein comprises adaptor sequences which comprise a binding moiety capable of binding to a solid support. In certain aspects, said binding moiety comprises biotin and solid support comprises streptavidin. In certain aspects, binding protein comprises adaptor sequences which are not compatible with downstream amplification and sequencing.

In certain aspects, denaturing comprises heat denaturing. In certain aspects, heat denaturing comprises application of heat above 70° C., 75° C., 80° C., 85° C., 90° C., 91° C., 92° C., 93° C., 94° C., or above 95° C. In certain aspects, renaturing comprises lowering the denaturation temperature to a temperature of about 40° C. to about 65° C. for a sufficient period of time to renature abundant nucleic acid species. In certain aspects, said sufficient period of time comprises about 30 minutes to about 24 hours. In certain aspects, denaturing comprises chemical denaturing.

In certain aspects, the method further comprises sequencing the separated less abundant nucleic acid species. In certain aspects, the library comprises genomic DNA. In certain aspects, the library comprises randomly sheared DNA. In certain aspects, the library comprises double-stranded cDNA. In certain aspects, the nucleic acids in the library comprise adaptor sequences ligated to the ends of the nucleic acids. In certain aspects, the adaptor sequences comprise one or more of: amplification priming binding region, sequencing primer binding region, and promotor sequences for in vitro transcription. In certain aspects, said abundant nucleic acid species comprise highly repetitive sequences. In certain aspects, said library comprises nucleic acid from a single cell or a small group of cells. In certain aspects, said abundant nucleic acid species comprise host sequences and said less abundant nucleic acid species comprise pathogen content. In certain aspects, said abundant nucleic acid species comprise duplicate libraries in a sequencing library. In certain aspects, the library comprises genomic RNA.

3 BRIEF DESCRIPTION OF THE DRAWINGS

4 DESCRIPTION

Figure 1A:
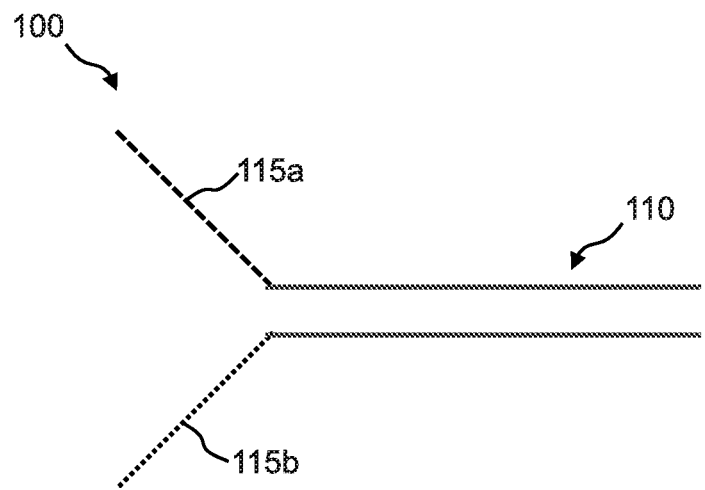
FIG. 1A illustrates a schematic diagram of an example of a forktail transposon.

The presently disclosed subject matter is related to U.S. Patent Pub. No. 20050153333, entitled "Selective terminal tagging of nucleic acids," published on Jul. 14, 2005; U.S. Patent Pub. No. 20100297643, entitled "Terminus-specific DNA modification using random-sequence template oligonucleotides," published on Nov. 25, 2010; and U.S. Patent Pub. No. 20140194324, entitled "Sample preparation of a solid support," published on Jul. 10, 2014, the entire disclosures of which are incorporated herein by reference.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein, the term "about" means+/−10%.

As used herein, the term "elevated temperature" means a temperature above 40° C. In some embodiments, the elevated temperature is within the range of about: 40° C.-95° C., 45° C.-90° C., or 50° C.-70° C. In some embodiments, the elevated temperature is about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95° C., or more.

As used herein, the terms "Affinity binding substances" or "affinity binding molecules" or "affinity molecules" mean molecules that have affinity for and "bind" to each other under certain conditions, referred to as "binding conditions", to form a "specific binding pair." For example, biotin and streptavidin, biotin and avidin, or digoxigenin and a specific antibody that binds digoxigenin are examples of "specific binding pairs," with the members of each specific binding pair comprising "affinity binding molecules" or "affinity binding substances" or "affinity molecules." Affinity binding molecules (e.g., biotin and/or streptavidin) can be covalently joined or conjugated, or non-covalently bound, to other molecules (e.g., to RNA or DNA) or to a solid surface using methods known in the art (e.g., using reagents and methods as described in Avidin-Biotin Chemistry: A Handbook, by D. Savage et al., Pierce Chemical Company, 1992, and in Handbook of Fluorescent Probes and Research Products, Ninth Edition, by R. P. Hoagland, Molecular Probes, Inc., and in BIOCONJUGATE Techniques, by Greg T. Hermanson, Published by Academic Press, Inc., San Diego, Calif., 1996). Affinity molecules that are conjugated to DNA or RNA can also be synthesized using an oligonucleotide synthesizer using reagents and methods known in the art. The term "binding" according to the present invention means the interaction between an affinity molecule and an affinity binding substance as a result of non-covalent bonds, such as, but not limited to, hydrogen bonds, hydrophobic interactions, van der Waals bonds, and ionic bonds. Without being bound by theory, it is believed in the art that these kinds of non-covalent bonds result in binding, in part due to complementary shapes or structures of the molecules involved in the specific binding pair. Based on the definition for "binding," and the wide variety of affinity binding molecules or specific binding pairs, it is clear that binding conditions vary for different specific binding pairs. Those skilled in the art can easily find or determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports)

in a sample. In certain cases, the specificity might also involve, or might be due to, a significantly more rapid association of affinity binding molecules than with other substances and components in a sample.

The terms "tag" and "tag domain" as used herein refer to a portion or domain of a polynucleotide that exhibits a sequence for a desired intended purpose or application. Some embodiments presented herein include a transposome complex comprising a polynucleotide having a 3' portion comprising a transposon end sequence, and tag comprising a tag domain. Tag domains can comprise any sequence provided for any desired purpose. For example, in some embodiments, a tag domain comprises one or more restriction endonuclease recognition sites. In some embodiments, a tag domain comprises one or more regions suitable for hybridization with a primer for a cluster amplification reaction. In some embodiments, a tag domain comprises one or more regions suitable for hybridization with a primer for a sequencing reaction. It will be appreciated that any other suitable feature can be incorporated into a tag domain. In some embodiments, the tag domain comprises a sequence having a length between 5 and 200 bp. In some embodiments, the tag domain comprises a sequence having a length between 10 and 100 bp. In some embodiments, the tag domain comprises a sequence having a length between 20 and 50 bp. In some embodiments, the tag domain comprises a sequence having a length between 5, 6, 7, 8, 9, 10, 20, 30, 40, 50, 60, 70, 80, 90, 100, 150 and 200 bp.

As used herein, the term "target nucleic acid" means any nucleic acid of interest.

Nucleic Acid

As used herein, nucleic acids can include single stranded, double stranded, and/or partially double stranded DNA; single stranded, double stranded, and/or partially double stranded cDNA; products of whole genome amplification (WGA); single stranded, double stranded; and/or partially double stranded RNA; peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof. In a preferred embodiment, genomic DNA fragments or amplified copies thereof are used as nucleic acids. In another preferred embodiment, cDNA, mitochondrial DNA or chloroplast DNA is used.

Nucleic acid can comprise any nucleotide sequence. In some embodiments, the nucleic acid comprises homopolymer sequences. A nucleic acid can also include repeat sequences. Repeat sequences can be any of a variety of lengths including, for example, 2, 5, 10, 20, 30, 40, 50, 100, 250, 500 or 1000 nucleotides or more. Repeat sequences can be repeated, either contiguously or non-contiguously, any of a variety of times including, for example, 2, 3, 4, 5, 6, 7, 8, 9, 10, 15 or 20 times or more.

In some embodiments, the length of the nucleic acids is about 20 bp, 30 bp, 40 bp, 50 bp, 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, 2500 bp, 2600 bp, 2700 bp, 2800 bp, 2900 bp, 3000 bp, 3100 bp, 3200 bp, 3300 bp, 3400 bp, 3500 bp, 3600 bp, 3700 bp, 3800 bp, 3900 bp, 4000 bp, 4100 bp, 4200 bp, 4300 bp, 4400 bp, 4500 bp, 4600 bp, 4700 bp, 4800 bp, 4900 bp, 5000 bp, 10000 bp, 30000 bp, 40000 bp, 50000 bp, 60000 bp, 70000 bp, 80000 bp, 90000 bp, 100 kbp (kilo base pair), 200 kbp, 300 kbp, 400 kbp, 500 kbp, 600 kbp, 700 kbp, 800 kbp, 900 kbp, 1 mbp (mega base pair), 2 mbp, 3 mbp, 4 mbp, 5 mbp, 6 mbp, 7 mbp, 8 mbp, 9 mbp, 10 mbp or longer.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Nucleic acids can be obtained from any source. For example, nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Thermus aquaticus, Thermococcus litoralis*, and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human).

Nucleic acid may be obtained from a biological sample. The term "biological sample" as used herein includes samples such as cell lysates, intact cells, organisms, organs, tissues and bodily fluids. "Bodily fluids" may include, but are not limited to, blood, dried blood, clotted blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin (i.e., a cellular sample made to be acellular).

In some embodiments, the biological sample can be from a human or from a non-human origin. In some embodiments, the biological sample can be from a human patient. In some embodiments, the biological sample can be from a newborn human.

The term "Plasma" as used herein refers to acellular fluid found in blood. "Plasma" may be obtained from blood by removing whole cellular material from blood by methods known in the art (e.g., centrifugation, filtration, and the like).

Nucleic acids can be enriched for certain sequences of interest using various methods well known in the art.

Examples of such methods are provided in Int. Pub. No. WO/2012/108864, which is incorporated herein by reference in its entirety.

Nucleic Acid Binding Protein

As used herein, the term "nucleic acid binding protein" means a protein binds to nucleic acids, for example, single stranded, double stranded, and/or partially double stranded DNA; single stranded, double stranded, and/or partially double stranded cDNA; products of whole genome amplification (WGA); single stranded, double stranded; and/or partially double stranded RNA; peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof.

In some embodiments, the nucleic acid binding protein binds specifically to double stranded nucleic acids. In some embodiments, the nucleic acid binding protein binds specifically to double stranded DNA. In some embodiments, the nucleic acid binding protein binds specifically to double stranded RNA. In some embodiments, the nucleic acid binding protein binds specifically to single stranded DNA. In some embodiments, the nucleic acid binding protein binds specifically to single stranded RNA. In some embodiments, the nucleic acid binding protein binds to specific nucleic acid sequences, for example, certain restriction endonucleases.

In some embodiments, the nucleic acid binding protein has enzymatic activity. In some embodiments, the enzymatic activity may be a DNA altering activity such a nuclease activity, recombinase activity, ligase activity, kinase activity, gyrase activity, polymerase activity, transposase activity. In some embodiments, the nucleic acid binding protein requires cofactors, for example, ATP, NADP, S-adenosyl-L-methionine, metal ions, e.g., $Mg^{2+}$, $Mn^{2+}$, $Co^{2+}$, $Ca^{2+}$, $Zn^{2+}$, $Al^{3+}$. In some embodiments, the enzymatic activity requires cofactors. In some embodiments, the nucleic acid binding protein can bind to nucleic acids in the absence of cofactors. In some embodiments, the nucleic acid binding protein with an enzymatic activity can bind to the nucleic acid in the absence of cofactors.

In some embodiments, the nucleic acid binding protein can be from a thermophilic organisms, for example, *Thermus aquaticus*, *Thermococcus litoralis*. Examples of other thermophilic organisms are disclosed in M T Madigan, J M Martinko & J Parker (1997) Brock Biology of Microorganisms. Eighth edition. Prentice Hall; Extremophiles; Special issue of Federation of European Microbiological Societies (FEMS) Microbiology Reviews 18, Nos. 2-3; May 1996, which are incorporated by reference herein in its entirety. In some embodiments, the nucleic acid binding protein can be modified to withstand elevated temperature. In some embodiments, the nucleic acid binding proteins can be fused with other proteins or peptides such that the altered protein are stable at elevated temperature.

Exemplary nucleic acid binding proteins that binds to double stranded DNA include, but are not limited to: transposases, restriction endonucleases, transcription factors, DNA dependent RNA polymerases.

Exemplary restriction endonucleases are provided in the Table below.

| Enzyme | Source | Recognition Sequence | Cut |
|---|---|---|---|
| EcoRI | *Escherichia coli* | 5'GAATTC<br>3'CTTAAG | 5'---G     AATTC---3'<br>3'---CTTA     G---5' |
| EcoRI | *Escherichia coli* | 5'CCWGG<br>3'GGWCC | 5'---  CCWGG---3'<br>3'---GGWCC  ---5' |
| BamHI | *Bacillus amyloliquefaciens* | 5'GGATCC<br>3'CCTAGG | 5'---G  GATCC---3'<br>3'---CCTAG  G---5' |
| HindIII | *Haemophilus influensae* | 5'AAGCTT<br>3'TTCGAA | 5'---A  AGCTT---3'<br>3---TTCGA  A---5' |
| TaqI | *Thermus aquaticus* | 5'TCGA<br>3'AGCT | 5'---T  CGA---3'<br>3'---AGC  T---5' |
| NotI | *Nocardia otitidis* | 5'GCGGCCGC<br>3'CGCCGGCG | 5'---GC  GGCCGC---3'<br>3'---CGCCGG  CG---5' |
| HinFI:"Hin"FI | *Haemophilus influenzae* | 5'GANTC<br>3'CTNAG | 5'---G  ANTC---3'<br>3'---CTNA  G---5' |
| Sau3AI | *Staphylococcus aureus* | 5'GATC<br>3'CTAG | 5'---  GATC---3'<br>3'---CTAG  ---5' |
| PvuII* | *Proteus vulgaris* | 5'CAGCTG<br>3'GTCGAC | 5'---CAG  CTG---3'<br>3'---GTC  GAC---5' |
| SmaI* | *Serratia marcescens* | 5'CCCGGG<br>3'GGGCCC | 5'---CCC  GGG---3'<br>3'---GGG  CCC---5' |
| HaeIII* | *Haemophilus aegyptius* | 5'GGCC<br>3'CCGG | 5'---GG  CC---3'<br>3'---CC  GG---5' |
| HgaI[68] | *Haemophilus gallinarum* | 5'GACGC<br>3'CTGCG | 5'---NN  NN---3'<br>3'---NN  NN---5' |
| AluI* | *Arthrobacter luteus* | 5'AGCT<br>3'TCGA | 5'---AG  CT---3'<br>3'---TC  GA---5' |

| Enzyme | Source | Recognition Sequence | Cut |
|---|---|---|---|
| EcoRV* | Escherichia coli | 5'GATATC<br>3'CTATAG | 5'---GAT    ATC---3'<br>3'---CTA    TAG---5' |
| EcoP15I | Escherichia coli | 5'CAGCAGN$_{25}$NN<br>3'GTCGTCN$_{25}$NN | 5'---CAGCAGN$_{25}$    NN---3'<br>3'---GTCGTCN$_{25}$NN    ---5' |
| KpnI[69] | Klebsiella pneumoniae | 5'GGTACC<br>3'CCATGG | 5'---GGTAC    C---3'<br>3'---C    CATGG---5' |
| PstI[69] | Providencia stuartii | 5'CTGCAG<br>3'GACGTC | 5'---CTGCA    G---3'<br>3'---G    ACGTC---5' |
| SacI[69] | Streptomyces achromogenes | 5'GAGCTC<br>3'CTCGAG | 5'---GAGCT    C---3'<br>3'---C    TCGAG---5' |
| SalI[69] | Streptomyces albus | 5'GTCGAC<br>3'CAGCTG | 5'---G    TCGAC---3'<br>3'---CAGCT    G---5' |
| ScaI*[69] | Streptomyces caespitosus | 5'AGTACT<br>3'TCATGA | 5'---AGT    ACT---3'<br>3'---TCA    TGA---5' |
| SpeI | Sphaerotilus natans | 5'ACTAGT<br>3'TGATCA | 5'---A    CTAGT---3'<br>3'---TGATC    A---5' |
| SphI[69] | Streptomyces phaeochromogenes | 5'GCATGC<br>3'CGTACG | 5'---GCATG    C---3'<br>3'---C    GTACG---5' |
| StuO*[70][71] | Streptomyces tubercidicua | 5'AGGCCT<br>3'TCCGGA | 5'---AGG    CCT---3'<br>3'---TCC    GGA---5' |
| XbaI[69] | Xanthomonas badrii | 5'TCTAGA<br>3'AGATCT | 5'---T    CTAGA---3'<br>3'---AGATC    T---5' |

The restriction endonucleases are available commercially through New England Biolabs, Inc., MA, USA.

Exemplary transposases include but are not limited to transposases from Tn5 (NCBI Ref No. U00004.1, variants of Tn5), *Thermus aquaticus* (NCBI Ref No. WP_003044334.1).

Exemplary nucleic acid binding proteins that bind to single stranded DNA include single stranded DNA binding proteins (SSB) of *Escherichia coli* (NCBI Ref No. WP_012846861.1), bacteria phage T7 (NCBI Ref No. NP_041970.1), bacteria phage T5 (NCBI Ref No. YP_006950.1); replication protein A of *Xenopus laevis* (NCBI Ref No. NP_001081585.1), *Mus musculus* (NCBI Ref No. NP_080929.1), *Drosophila melanogaster* (NCBI Ref No. NP_524274.1), *Thermus aquaticus* (NCBI Ref No. EED09986.1), *Homo sapiens* (NCBI Ref No. NP_002936.1).

Exemplary nucleic acid binding proteins that bind to both single stranded and double stranded DNA include but are not limited to *Escherichia coli* recA (NCBI Ref No. YP_006777928.1), *Thermus aquaticus* recA (NCBI Ref No. WP_003043690.1).

Exemplary nucleic acid binding proteins that bind to RNA include but are not limited to RNA binding proteins, ribonucleases such as RNase A (binds to single stranded RNA), RNase III, RNase L, RNase P, RNase T1 (binds to single stranded RNA), RNase T2 (binds to single stranded RNA), RNase U2 (binds to single stranded RNA).

Exemplary nucleic acid binding proteins that bind to RNA-DNA hybrid include but are not limited to RNase H (e.g., HIV-1 RNase H, MMLV RNase H), Reverse transcriptases.

Transposomes

A "transposome" comprises an integration enzyme such as an integrase or transposase, and a nucleic acid comprising an integration recognition site, such as a transposase recognition site. In embodiments provided herein, the transposase can form a functional complex with a transposase recognition site that is capable of catalyzing a transposition reaction. The transposase may bind to the transposase recognition site and insert the transposase recognition site into a target nucleic acid in a process sometimes termed "tagmentation". In some such insertion events, one strand of the transposase recognition site may be transferred into the target nucleic acid. In one example, a transposome comprises a dimeric transposase comprising two subunits, and two non-contiguous transposon sequences. In another example, a transposome comprises a transposase comprises a dimeric transposase comprising two subunits, and a contiguous transposon sequence.

Exemplary transposases include, but are not limited to Mu, Tn10, Tn5, hyperactive Tn5 (Goryshin and Reznikoff, J. Biol. Chem., 273:7367 (1998)).

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wis.) comprises the following 19b transferred strand (sometimes "M" or "ME") and non-transferred strands: 5' AGAT-GTGTATAAGAGACAG 3', 5' CTGTCT CTTATACA-CATCT 3', respectively. ME sequences can also be used as optimized by a skilled artisan.

More examples of transposition systems that can be used with certain embodiments of the compositions and methods provided herein include *Staphylococcus aureus* Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include IS5, Tn10, Tn903, IS911, Sleeping Beauty, SPIN, hAT, PiggyBac, Hermes, TcBuster, AeBuster1, Tol2, and engineered versions of transposase family enzymes (Zhang et al., (2009) PLoS Genet. 5:e1000689. Epub 2009 Oct. 16; Wilson C. et al (2007) J. Microbiol. Methods 71:332-5).

Variants of Tn5 transposases, such as having amino acid substitutions, insertions, deletions, and/or fusions with other proteins or peptides are disclosed in U.S. Pat. Nos. 5,925, 545; 5,965,443; 7,083,980; 7,608,434; and U.S. patent application Ser. No. 14/686,961. The patents and the patent application are incorporated herein by reference in its entirety. In some embodiments, the Tn5 transposase comprise one or more substitutions at positions 54, 56, 372, 212, 214, 251, and 338 with respect to the wild type protein as disclosed in U.S. patent application Ser. No. 14/686,961. In some embodiments, the Tn5 wild-type protein or its variant can further comprise a fusion polypeptide. In some embodiments, the polypeptide domain fused to the transposase can comprise, for example, Elongation Factor Ts. Exemplary Tn5 transposases and its variants are shown in SEQ ID NOs: 1-22.

More examples of integrases that may be used with the methods and compositions provided herein include retroviral integrases and integrase recognition sequences for such retroviral integrases, such as integrases from HIV-1, HIV-2, SIV, PFV-1, RSV.

In one aspect, the invention provides methods of reducing the complexity of a nucleic acid library. The nucleic acid library may be, for example, a genomic DNA library or a double-stranded cDNA library prepared using mRNA or total RNA. In various embodiments, the methods of the invention use a modified Tn5 transposase to remove double-stranded DNA molecules from a mixture of single- and double-stranded DNA molecules to reduce the complexity of a DNA library. In one example, the transposase is Ts-Tn5. In another example, the transposase is EZ-Tn5™ (Illumina, Inc.).

In various embodiments, the methods of the invention use DNA reassociation kinetics following thermal denaturation to define populations of nucleic acid sequences, e.g., highly abundant (e.g., cDNA from rRNA), moderately abundant, and less abundant or rare sequences (e.g., cDNA from mRNA). The rate at which a particular sequence will reassociate is proportional to the number of copies of that sequence in the DNA sample. For example, highly-repetitive (abundant) sequence will reassociate rapidly, while complex sequences (less abundant) will reassociate more slowly and remain single-stranded for a longer period of time.

In one embodiment, the methods of the invention provide for selective identification and sequence analysis of both the abundant and less abundant (e.g., rare) species of nucleic acids present in a sample. In one example, a biotinylated transposome is used to selectively tag and capture the more abundant DNA molecules in a DNA library thereby reducing the complexity of abundant sequences in the DNA library. The less abundant DNA molecules remain in the supernatant and may be readily processed for sequence analysis. The tagged and captured abundant DNA molecules may also be readily processed for subsequent analysis.

In another embodiment, the methods of the invention use transposome-based normalization to reduce the impact of abundant sequences (e.g., rRNA) in library sequence analysis.

In one application, Ts-Tn5 fusion transposases are used in the preparation of directional RNA-seq libraries for sequencing on next generation sequencing platforms (e.g., Illumina GAIIx or HiSeq platforms).

Solid Support

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads. In some embodiments, the beads can be color coded. For example, MicroPlex® Microspheres from Luminex, Austin, Tex. may be used. In some embodiments, the solid support comprise affinity binding molecules. Exemplary affinity binding molecules include, but are not limited to biotin-streptavidin, antigen-antibody, enzyme-substrate. In some embodiments, the beads comprise streptavidin.

The beads need not be spherical; irregular particles may be used. Alternatively or additionally, the beads may be porous. The bead sizes range from nanometers, i.e. about 10 nm, to millimeters in diameter, i.e. 1 mm, with beads from about 0.2 micron to about 200 microns being preferred, and from about 0.5 to about 5 micron being particularly preferred, although in some embodiments smaller or larger beads may be used. In some embodiments, beads can be about 0.1, 0.2, 0.3, 0.4, 0.5. 0.6, 0.7, 0.8, 0.9, 1, 1.5, 2, 2.5, 2.8, 3, 3.5, 4, 4.5, 5, 5.5, 6, 6.5, 7, 7.5, 8, 8.5, 9, 9.5, 10, 10.5, 15, 20, 25, 30, 35, 40, 45, 50, 55, 60, 65, 70, 75, 80, 85, 90, 95, 100, 150, or 200 µm in diameter.

Immobilizing Nucleic Acid Proteins to Solid Support

Methods for immobilizing proteins to solid support by covalent bonds are well known in the art. For example, a variety of surface chemistries can be used to immobilize a binding protein to a solid surface including covalent bonding of amine groups on proteins to aldehyde or epoxide groups on silanized glass surfaces, or other functional groups on a solid support (see Guo and Zhu, (2007) "The Critical Role of Surface Chemistry in Protein Microarrays" in Functional Protein Microarrays in Drug Discovery, Ed. Paul F. Predki, CRC Press, Chapter 4, pgs 53-71). Additionally, known methods can be used to attach a protein moiety to a solid support including, for example, as described in U.S. Pat. Nos. 8,022,013, 8,912,130, 7,977,476, 7,259,258, U.S. Patent Application Publication No. 20130059741, and PCT application publication WO/2001/041918, each of which is incorporated by reference in its entirety.

In some embodiments, the proteins, such as nucleic acid binding proteins can be immobilized on a solid support by non-covalent means, for example by the use of affinity binding molecules. In some embodiments, the nucleic acid binding protein is transposase. The transposons in the transposome complex may comprise biotin and the transposome complex can be immobilized on a solid support comprising streptavidin or neutravidin.

4.1 Sequencing Methods

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference. This approach is being commercialized by Solexa (now Illumina Inc.), and is also described in International Patent Pub. No. WO 91/06678 and International Patent Pub. No. WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type.

Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057,026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/0270305 and U.S. Patent Pub. No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Pub. No. 2013/0079232. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated materials of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Pub. No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference.

4.2 Ts-Tn5 Transposomes

The invention provides transposase fusion proteins comprising a modified Tn5 transposase and elongation factor Ts (Tsf). Ts is a protein tag that may be used to enhance the solubility of heterologous proteins expressed in a bacterial expression system, e.g., an E. coli expression system. Ts-Tn5 transposase has enhanced expression, solubility and purification yields compared to an unfused standard Tn5.

The Ts-Tn5 fusion protein may be assembled into a functional transposome complex comprising the fusion transposase and free or appended transposon ends (mosaic end (ME)). In one example, Ts-Tn5 is assembled into a functional "forktail" transposome complex. FIG. 1A illustrates a schematic diagram of an example of a forktail transposon 100. Forktail transposon 100 comprises mosaic end (ME) sequences 110. ME sequences 110 are Tn5 transposase recognition sequences used in the assembly of a transposome complex. ME sequences 110 is about 19 bp. ME sequences 110 is appended with adaptor sequences 115, e.g., adaptor sequences 115a and 115b. Adaptor sequences 115 are relatively short oligonucleotide sequences, e.g., about 14 nucleotides. Adaptor sequences 115 are sites for primer annealing in, for example, a PCR amplification protocol.

Forktail transposon 100 may be assembled into a functional forktail transposome (not shown). The forktail transposome complex may be used to tagment double-stranded cDNA in an RNA-seq library preparation protocol (e.g., a TotalScript™ RNA-seq library preparation protocol). Forktail transposon 100 obviates the need for an oligonucleotide replacement step in the current TotalScript™ RNA-seq protocol. Forktail transposon 100 may also be used in transposome complexes to eliminate the A-A and B-B fragments that are generated in existing Nextera transposition reactions (not shown). The relatively short length of adaptor sequences 115 limits the renaturation of common adaptor sequences in a denaturation/renaturation process, as described in more detail with reference to FIG. 8 and FIG. 9.

Figure 1B:
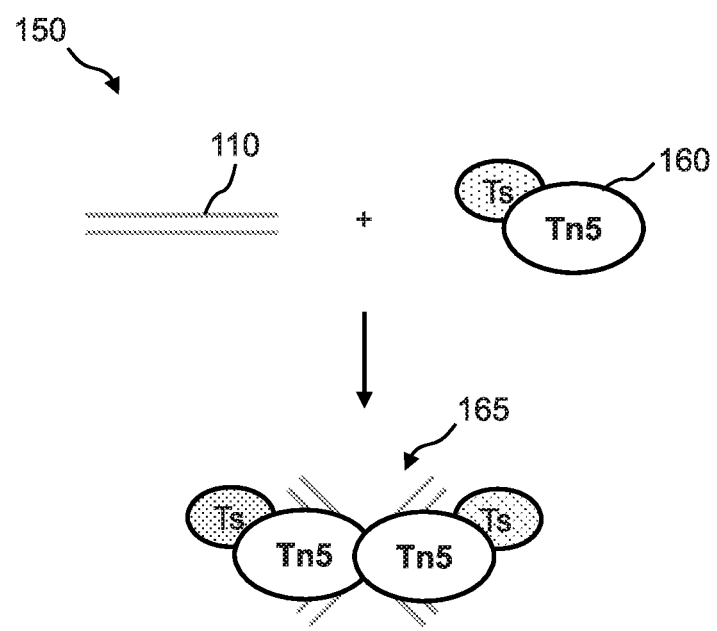
FIG. 1B illustrates a schematic diagram of assembling a Ts-Tn5 suicide transposome complex.

In another example, Ts-Tn5 transposase is assembled into a functional "suicide" transposome complex. FIG. 1B illustrates a schematic diagram 150 of assembling a Ts-Tn5 suicide transposome complex. In this example, free transposon ME sequences 110 are mixed with Ts-Tn5 transposase 160 to form an assembled suicide transposome complex 165. In this example, ME sequences 110 in suicide transposome complex 165 are not appended with specific adaptor sequences. Because ME sequences 110 are not appended with specific adaptor sequences, DNA fragmented and tagged using suicide transposome complex 165 are not available for subsequent amplification by specific adaptor-mediated PCR.

In one example, ME sequences 110 may be biotinylated and used to assemble a biotinylated transposome complex (not shown). The biotinylated transposome complex may comprise, for example, Ts-Tn5 transposase or EZ-Tn5 transposase. Because ME sequences 110 are biotinylated, double-stranded DNA fragmented and tagged using the biotinylated transposome complex may be recovered by affinity-capture for subsequent analysis by sequencing. The less abundant single-stranded DNA in a sample may be analyzed by sequencing the unbound fraction. An example of using a biotinylated transposome complex to reduce library complexity is described in more detail with reference to FIG. 5.

In another example, suicide transposome complex 165 may be used in a library normalization process to substantially reduce the amount of abundant nucleic acids (e.g., from rRNA) in a cDNA library, as described in more detail with reference to FIG. 8 and FIG. 9.

Figure 2A:
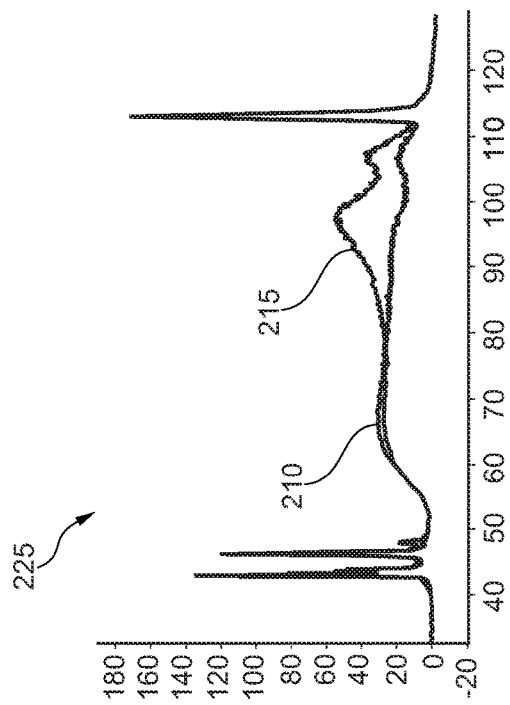
FIG. 2A shows a plot of the fragment size distribution of tagmented DNA prepared using transposomes comprising a standard TotalScript transposon and a standard Tn5 transposase.
Figure 2B:
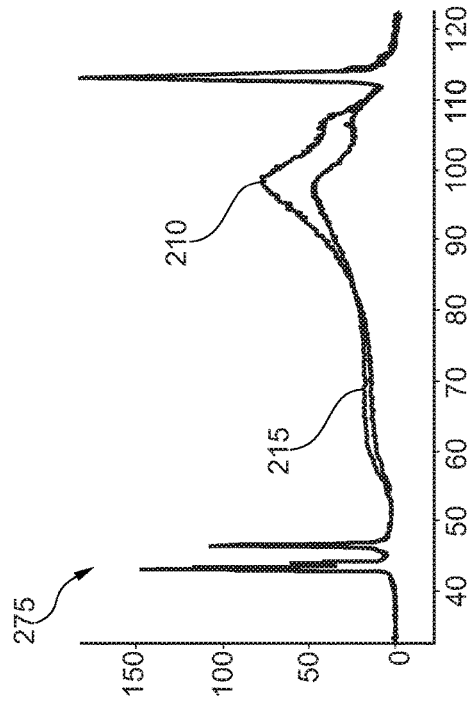
FIG. 2B shows a plot of the fragment size distribution of tagmented DNA prepared using transposomes comprising the forktail transposon of FIG. 1 and a standard Tn5 transposase.
Figure 2C:
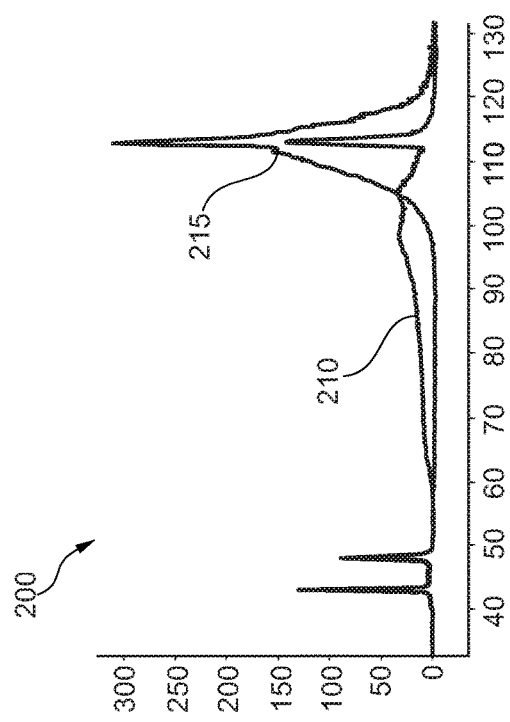
FIG. 2C shows a plot of the fragment size distribution of tagmented DNA prepared using transposomes comprising the standard TotalScript transposon and Ts-Tn5 transposase.
Figure 2D:
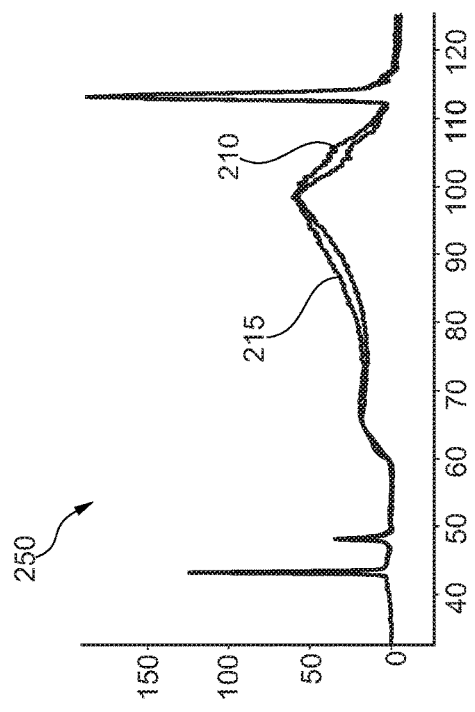
FIG. 2D shows a plot of the fragment size distribution of tagmented DNA prepared using transposomes comprising the forktail transposon of FIG. 1 and Ts-Tn5 transposase.

To evaluate the thermal stability of transposomes assembled with a standard Tn5 transposase or Ts-Tn5 transposase, DNA was tagmented using transposomes that were stored at −20° C. or stored at −20° C. and then incubated at 37° C. for 6 hours. Transposome complexes were assembled using TotalScript transposon sequences or forktail transposon 100 of FIG. 1. For each experiment, phage DNA (40 ng) was tagmented using transposomes that were stored at −20° C. or incubated at 37° C. for 6 hours. Tagmented DNA was then purified using DNA Clean & Concentrator™ columns (Zymo Research) and analyzed using the High Sensitivity DNA Assay (Agilent Technologies). FIG. 2A shows a plot 200 of the fragment size distribution of tagmented DNA prepared using transposomes comprising a standard TotalScript transposon and a standard Tn5 transposase. FIG. 2B shows a plot 225 of the fragment size distribution of tagmented DNA prepared using transposomes comprising forktail transposon 100 of FIG. 1 and a standard Tn5 transposase. FIG. 2C shows a plot 250 of the fragment size distribution of tagmented DNA prepared using transposomes comprising the standard TotalScript transposon and Ts-Tn5 transposase. FIG. 2D shows a plot 275 of the fragment size distribution of tagmented DNA prepared using transposomes comprising forktail transposon 100 of FIG. 1 and Ts-Tn5 transposase. Plot 200 of FIG. 2A, plot 225 of FIG. 2B, plot 250 of FIG. 2C, and plot 275 of FIG. 2D show a line 210 of the fragment size distribution of tagmented DNA prepared using transposomes stored at −20° C. Plots 200, 225, 250, and 275 also show a line 215 of the fragment size distribution of tagmented DNA prepared using transposomes stored at −20° C. and then incubated at 37° C. for 6 hours.

Referring now to FIG. 2A, line 210 of plot 200 shows that transposomes (i.e., comprising TotalScript transposon+Tn5 transposase) stored at −20° C. and then used in a tagmentation reaction generate a range of fragment sizes. Line 215 of plot 200 shows transposomes (i.e., comprising TotalScript transposon+Tn5 transposase) stored at −20° C. and then incubated at 37° C. for 6 hours prior to a tagmentation reaction are substantially less active in fragmenting the DNA.

Referring now to FIG. 2B, line 215 of plot 225 shows that transposomes (i.e., comprising forktail transposon+Tn5 transposase) stored at −20° C. and incubated at 37° C. for 6 hours prior to a tagmentation reaction are more active in tagmenting DNA compared to the transposomes (i.e., comprising TotalScript transposon+Tn5 transposase) of FIG. 2A incubated at 37° C. for 6 hours prior to tagmentation.

Referring now to FIG. 2C, plot 250 shows that transposomes (i.e., TotalScript transposon+Ts-Tn5 transposase) stored at −20° C. (line 210) and transposomes stored at −20° C. and incubated at 37° C. for 6 hours prior to a tagmentation reaction (line 215) have essentially the same level of tagmentation activity.

Referring now to FIG. 2D, plot 275 shows that transposomes (i.e., forktail transposon+Ts-Tn5 transposase) stored at −20° C. (line 210) and transposomes stored at −20° C. and incubated at 37° C. for 6 hours prior to a tagmentation reaction (line 215) have essentially the same level of tagmentation activity.

Referring now to FIGS. 2A through 2D, the data show that transposomes comprising Ts-Tn5 transposase (i.e., TotalScript transposon+Ts-Tn5 transposase and forktail transposon+Ts-Tn5) are more stable at 37° C. (i.e., they have increased thermal stability) compared to transposomes comprising the standard Tn5 transposase.

Figure 3A:
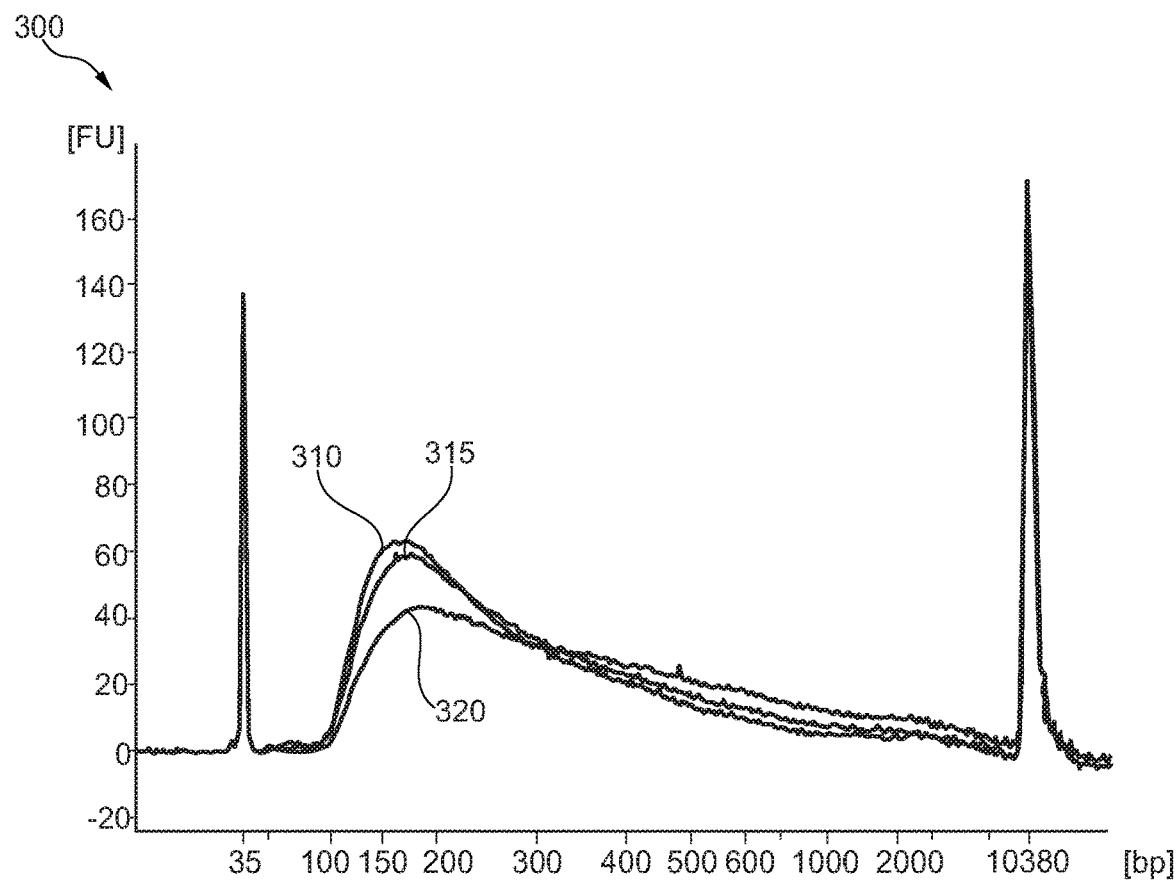
FIG. 3A shows a plot of the fragment size distribution of tagmented DNA prepared at elevated (>55° C.) temperatures using Ts-Tn5 transposomes.
Figure 3B:
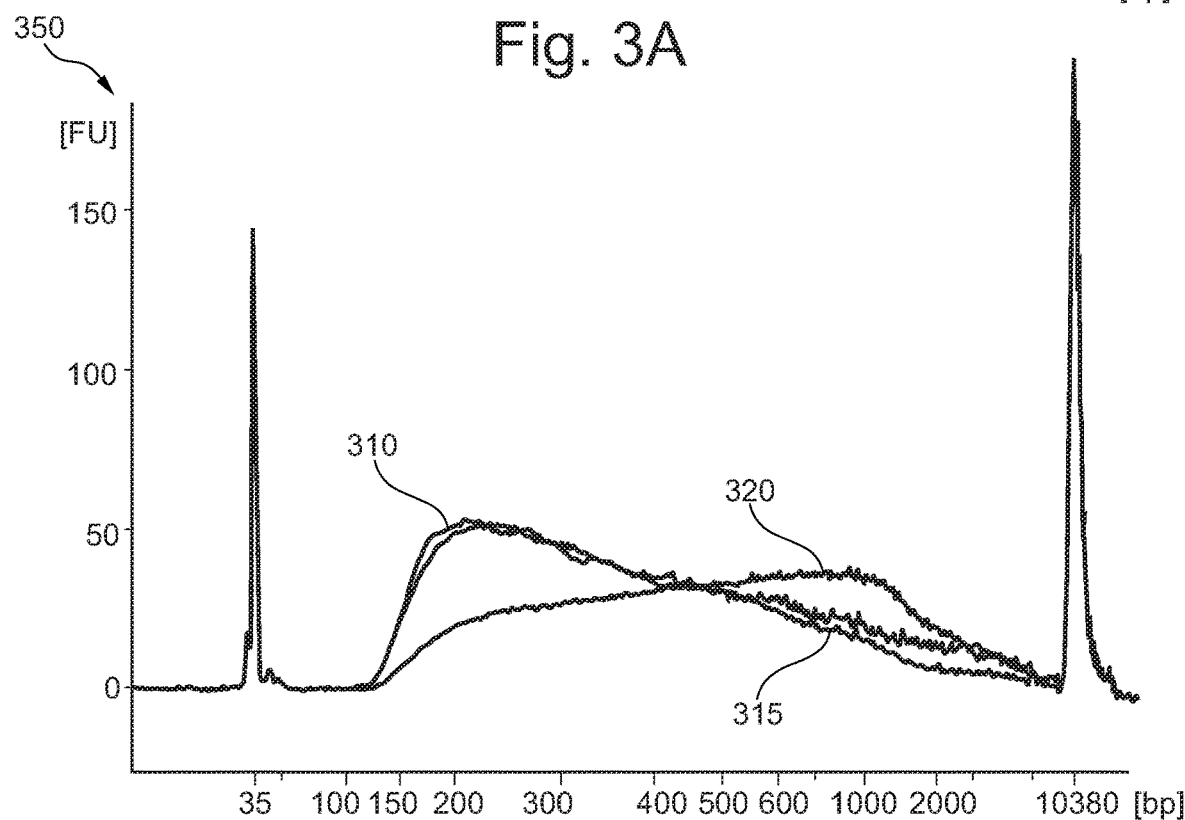
FIG. 3B shows a plot of the fragment size distribution of tagmented DNA prepared at elevated (>55° C.) temperatures using a standard Tn5 transposome (TDE1)

FIG. 3A shows a plot 300 of the fragment size distribution of tagmented DNA prepared at elevated (>55° C.) temperatures using Ts-Tn5 transposomes. In this example, the Ts-Tn5 transposome comprises free transposon ME sequences and Ts-Tn5 transposase. FIG. 3B shows a plot 350 of the fragment size distribution of tagmented DNA prepared at elevated (>55° C.) temperatures using a standard Tn5 transposome (TDE1). For each experiment, tagmented DNA was prepared using 50 ng of human genomic DNA (Coriell), 2 pmoles of transposome, and Nextera TD buffer in a total reaction volume of 40 μL. Reactions were incubated at 57, 65, and 70° C. for 5 minutes. Tagmented DNA was then purified using DNA Clean & Concentrator™ columns (Zymo Research) and analyzed using the High Sensitivity DNA Assay (Agilent Technologies).

Plot 300 of FIG. 3A and plot 350 of FIG. 3B show a line 310 of the fragment size distribution of DNA tagmented at 57° C., a line 315 of the fragment size distribution of DNA tagmented at 65° C., and a line 320 of the fragment size distribution of DNA tagmented at 70° C. Referring now to plot 300 of FIG. 3A, the data show that at 57° C. (line 310), 65° C. (line 315), and 70° C. (line 320) the Ts-Tn5 transposome tagments the DNA generating lower molecular weight fragments. Referring now to plot 350 of FIG. 3B, the data show that at 57° C. (line 310) and 65° C. (line 315) the standard Tn5 transposome tagments DNA generating lower molecular weight fragments. At 70° C. (line 320), the standard Tn5 transposome has substantially reduced tagmentation activity.

Figure 4:
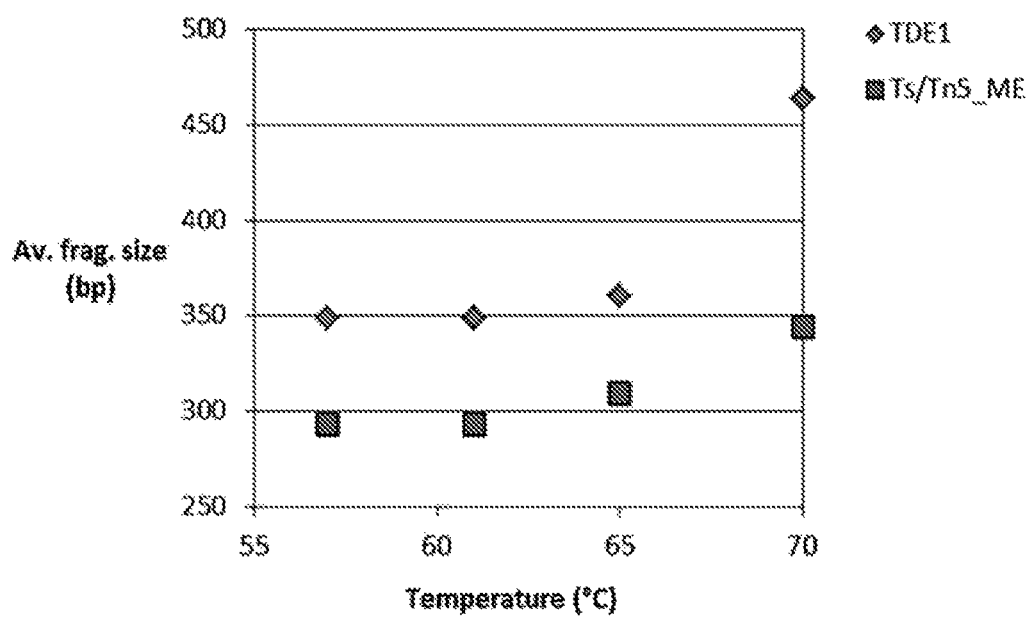
FIG. 4 shows a plot of DNA fragment size verses tagmentation reaction temperature for the tagmented DNA of FIG. 3A and FIG. 3B.

FIG. 4 shows a plot 400 of DNA fragment size verses tagmentation reaction temperature for the tagmented DNA of FIG. 3A and FIG. 3B. The data show that the average fragment size correlates with reaction temperature and the level of transposome activity.

Referring to FIG. 3A, FIG. 3B, and FIG. 4, the data show that the activity of the Ts-Tn5 transposome is more thermostable compared to the standard Tn5 transposome.

4.3 Selective Identification and Sequence Analysis of Abundant and Less Abundant Nucleic Acids In one embodiment, the methods of the invention provide for selective identification and sequence analysis of both the abundant and less abundant (e.g., rare) species of in a DNA library. The DNA library may be, for example, a genomic DNA library or a double-stranded cDNA library prepared using total RNA or mRNA. The genomic DNA library may be, for example, a transposome-generated library or a randomly sheared and end repaired adapter-ligated library comprising a defined adapter sequence at its ends. Similarly, a double-stranded cDNA library may also have a defined adapter sequence at its ends, such as in a Script-Seq or ExactSTRART generated library. The defined adaptor sequence may correspond to sequences related to primers for sequencing and/or for cluster generation in a flow cell or constitute promoter sequences for in vitro transcription.

IN one embodiment, the methods of the invention are carried out at elevated temperature. In one embodiment, the methods of the invention use a transposase from hemophilic organisms, for example, *Thermus aquaticus, Thermococcus litoralis*.

In one embodiment, the methods of the invention use a transposome (e.g., a Ts-Tn5-ME transposome or an EZ-Tn5™ ME-Transposome (Illumina, Inc) to selectively remove abundant double-stranded DNA molecules from a sample, thereby reducing the complexity of abundant sequences in the sample. A transposome specifically targets double-stranded DNA. Single-stranded DNA, RNA (single- or double-stranded), or RNA: DNA hybrids are not recognized as targets by the transposome. Therefore, a transposome may be used to selectively target double-stranded DNA molecules in a mixture of double-stranded and single-stranded DNA molecules. For example, when a complex mixture such as a genomic DNA library or a double-stranded cDNA library is denatured by heat and subsequently cooled, highly abundant sequences more rapidly form double-stranded structures and are recognized as targets for transposition. The transposome may contain appropriately tagged (e.g., a biotin tag) and/or appended transposon ends enabling affinity-capture of the targeted double-stranded sequences. The less abundant single-stranded nucleic acids remain in the supernatant and may be readily processed for sequence analysis. The tagged and captured abundant DNA molecules may also be readily processed for subsequent analysis.

Figure 5:
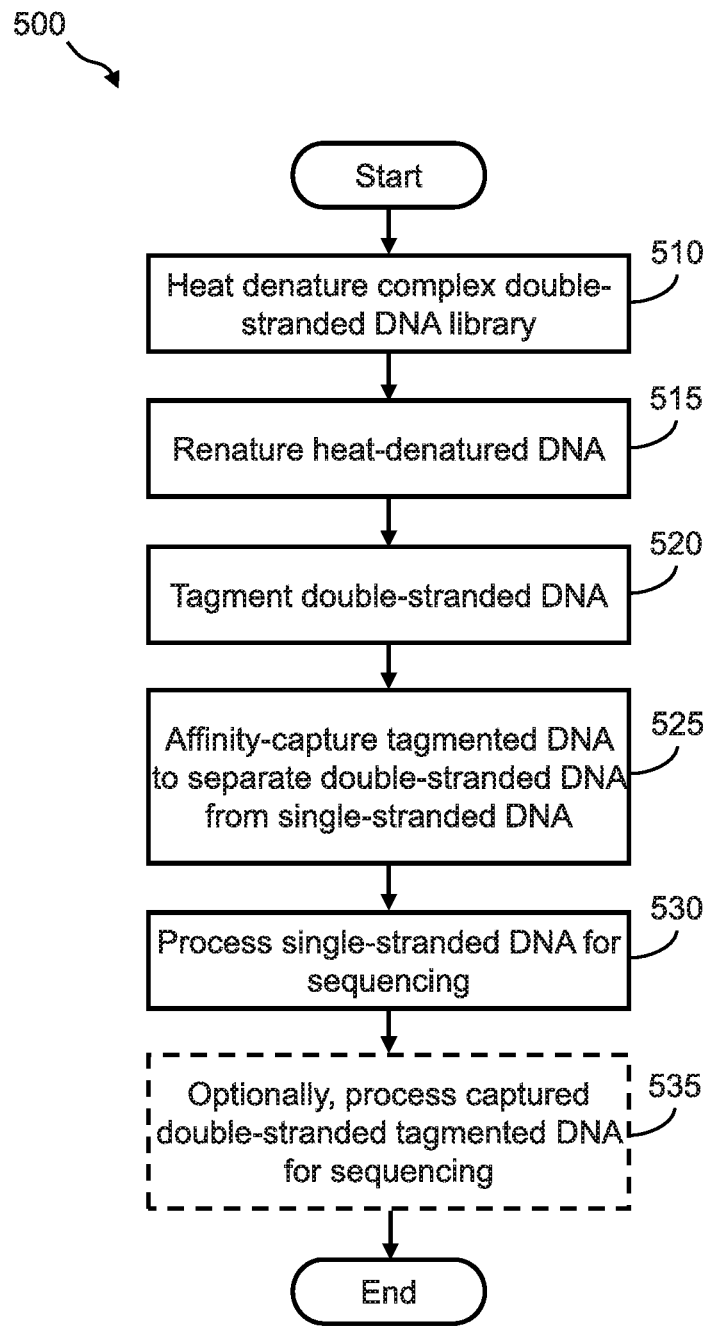
FIG. 5 illustrates a flow diagram of an example of a method of reducing the abundance of double-stranded DNA in a complex library by simultaneously fragmenting and tagging the end(s) of double-stranded DNA using a transposome.

FIG. 5 illustrates a flow diagram of an example of a method 500 of reducing the abundance of double-stranded DNA in a complex library by simultaneously fragmenting and tagging the end(s) of double-stranded DNA using a transposome. Method 500 includes, but is not limited to, the following steps.

At a step 510, a complex double-stranded DNA library is denatured. The DNA library may be, for example, a genomic DNA library or a double-stranded cDNA library prepared using mRNA or total RNA. In one example, the DNA library is denatured using the application of heat at a sufficient temperature (e.g., from about 80° C. to about 95° C.) to create single-stranded DNA.

At a step 515, the heat-denatured DNA is renatured. For example, the heat-denatured DNA is renatured by lowering the denaturation temperature (about 80° C. to about 95° C.) to from about 40° C. to about 65° C. and incubated at about 55° C. for an extended period of time (e.g., from about 30 minutes to about 24 hours) sufficient to renature abundant nucleic acid species.

At a step 520, double-stranded DNA in the renatured mixture is tagmented. For example, a transposome is added to the renatured mixture and incubated at about 55° C. for up to about 10 minutes. The transposome may be, for example, a Ts-Tn5-ME transposome or an EZ-TN5™ ME-Transposome (Illumina, Inc). The ME sequence in the transposome comprises an affinity tag such as biotin, whereby tagmentation of double-stranded DNA results in biotin-tagged double-stranded DNA. In another example, the biotinylated ME sequences may be appended with adaptor sequences that may be used to subsequently amplify the fragmented and tagged double-stranded DNA for sequencing.

At a step 525, the fragmented and biotin-tagged double-stranded DNA is affinity captured to separate double-stranded DNA from single-stranded DNA. In one example, the biotin-tagged double-stranded DNA is captured using streptavidin-agarose. In another example, the biotin-tagged double-stranded DNA is captured using magnetic beads comprising streptavidin-agarose. Following affinity capture of the more abundant double-stranded DNA, the less abundant, non-biotinylated single-stranded DNA is retained in the supernatant fraction.

At a step 530, the less abundant single-stranded DNA retained in the supernatant fraction is processed for subsequent sequencing. For example, the less abundant DNA may be tagged at the ends, for subsequent amplification and sequencing, either directly (e. g., Terminal transferase) or by 3'-terminal tagging according to the methods described in the U.S. Patent Pub. No. 20050153333 and/or the U.S. Patent Pub. No. 20100297643.

At an optional step 535, the captured double-stranded tagmented DNA is processed for amplification and sequencing. Method 500 ends.

To demonstrate the specificity of transposome-mediated fragmentation of double-stranded DNA in a mixture of double-stranded DNA and single-stranded DNA, tagmentation reactions were performed using single-stranded M13mp19 phage DNA and double-stranded pUC19 plasmid DNA.

Figure 6:
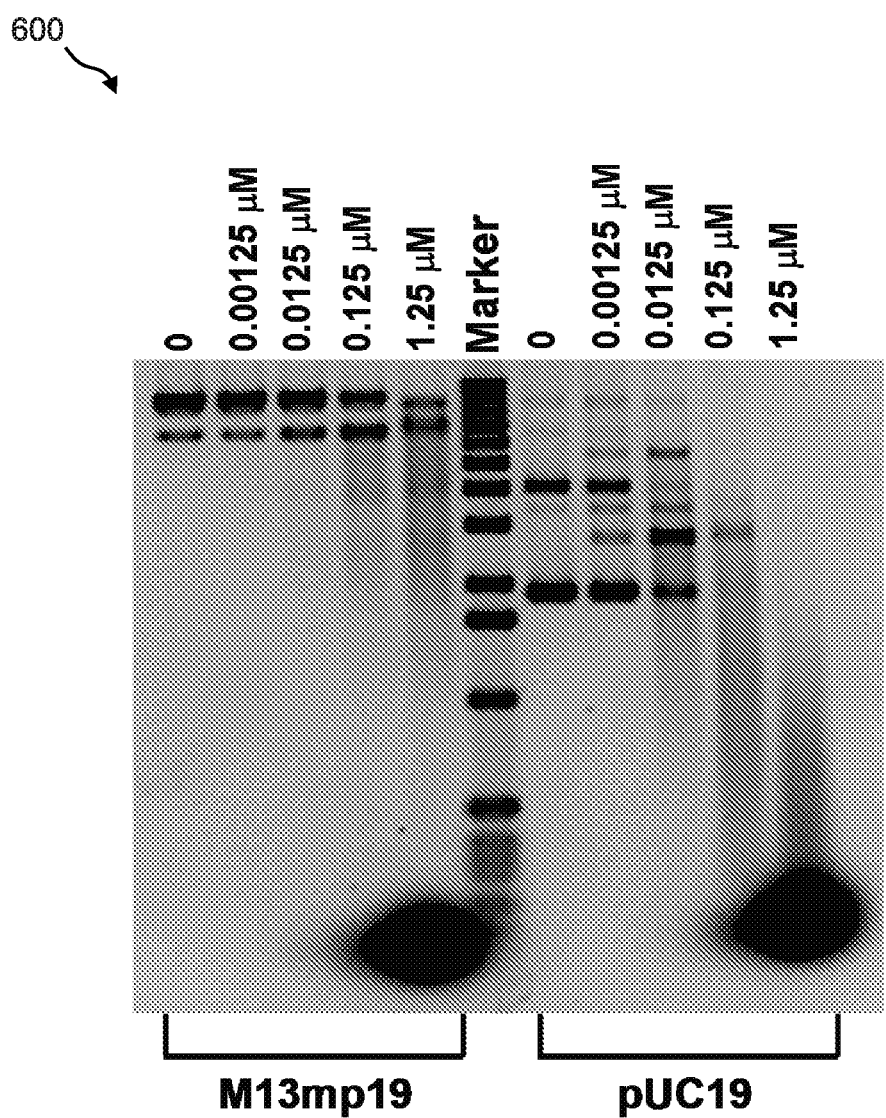
FIG. 6 shows a photograph of an agarose gel of the fragmentation of single-stranded M13mp19 DNA and double-stranded pUC19 DNA by EZ-Tn5™ ME-Transposome.

FIG. 6 shows a photograph 600 of an agarose gel of the fragmentation of single-stranded M13mp19 DNA and double-stranded pUC19 DNA by EZ-Tn5™ ME-Transposome. An aliquot (20 ng) of single-stranded M13mp19 DNA or double-stranded pUC19 DNA in a final volume of 9 μL of buffer containing 20 mM Tris.HCl (pH 8.0) and 5 mM MgCl$_2$ were pre-incubated at 55° C. for 1 minute. After the incubation period, 1 μL of EZ-Tn5™ ME-Transposome was added to obtain a final concentration ranging from 0.00125 μM to 1.25 μM. All transposome dilutions were performed in Transposome Storage buffer (50 mM Tris.HCl pH 7.5, 50% glycerol, 0.1 mM EDTA, 1 mM DTT, 500 mM NaCl, 0.5% NP40 and 0.5% Tween 20). Control reactions used 1 μL of Transposome Storage buffer. The mixture was incubated at 55° C. for 5 min and the reaction was stopped by adding 2 μL of stop buffer (20 mM Tris.HCl pH8.0, 15% Sucrose, 66 mM EDTA, 1 SDS, 0.9% Orange G) and incubated at 70° C. for 10 minutes. An aliquot (5 μL) of each reaction was analyzed on a 1% agarose gel and the nucleic acids were visualized by staining with SYBR-gold. The data show that double-stranded pUC19 DNA is fragmented by the EZ-Tn5™-ME transposome; 20 ng of double-stranded pUC19 DNA is fragmented, essentially to completion using 0.125 μM EZ-Tn5 ME-Transposome. The data also show that the single-stranded M13mp19 DNA is relatively intact (un-fragmented) compared to the double-stranded pUC19 DNA.

Figure 7:
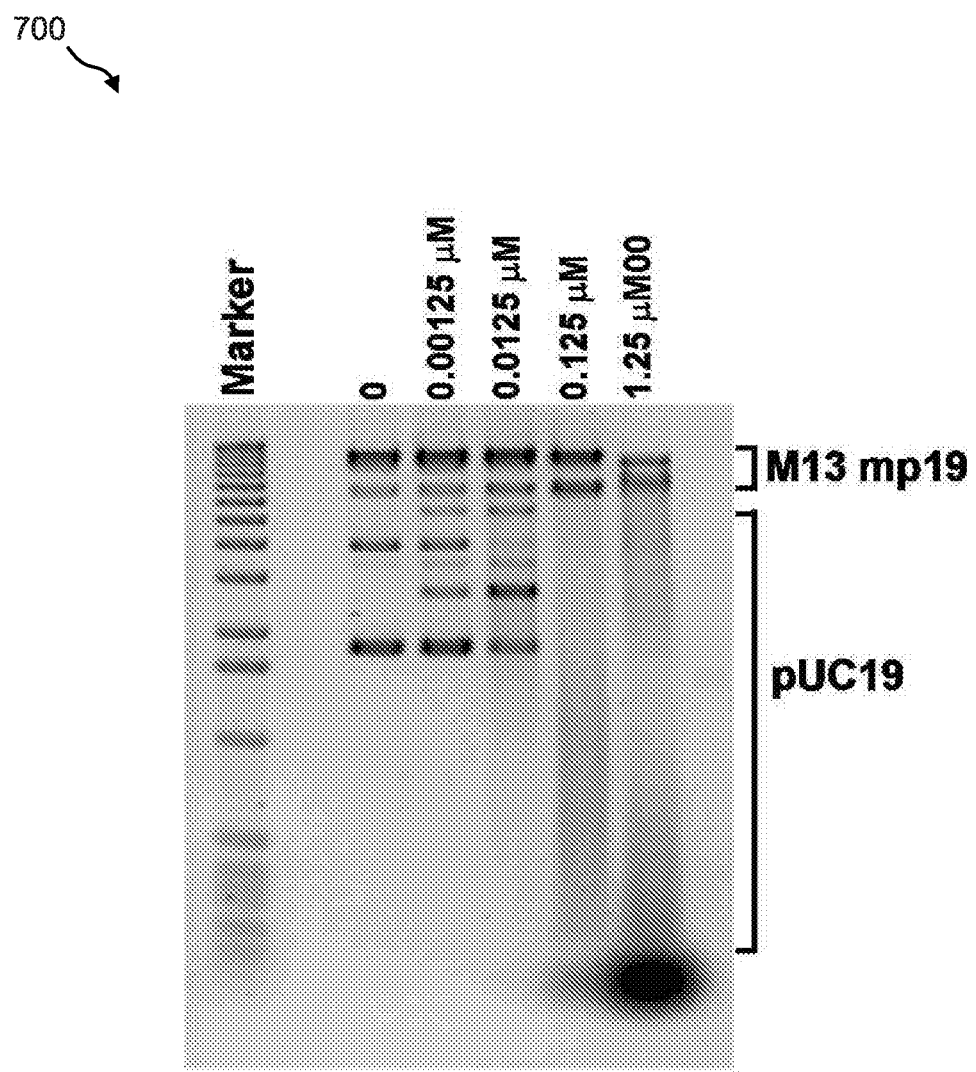
FIG. 7 shows a photograph of an agarose gel of the specific fragmentation of double-stranded pUC19 DNA in a mixture comprising single-stranded M13mp19 DNA and double-stranded pUC19 DNA.

FIG. 7 shows a photograph 700 of an agarose gel of the specific fragmentation of double-stranded pUC19 DNA in a mixture comprising single-stranded M13mp19 DNA and double-stranded pUC19 DNA. The reaction conditions are essentially the same as described with reference to FIG. 6 except that 20 ng of single-stranded M13mp19 DNA and 20 ng of double-stranded pUC19 DNA were mixed together and incubated prior to the tagmentation reaction. An aliquot (5 μL) of each reaction was analyzed on a 1% agarose gel and the nucleic acids were visualized by staining with SYBR-gold. The data show that reaction mixtures comprising 20 ng each of single- and double-stranded DNA with up to 0.125 μM EZ-Tn5 ME-Transposome results in specific recognition of the double-stranded pUC19 as a target and its subsequent fragmentation. The single-stranded M13mp19 DNA is left relatively intact under these conditions.

4.4 RNA-Seq Library Normalization

In one embodiment, Ts-Tn5 fusion transposases are used in the preparation of a directional RNA-seq library for sequencing on next generation sequencing platforms (e.g., Illumina GA or HiSeq platforms). For example, a first transposome complex comprising forktail transposon 100 of FIG. 1A and Ts-Tn5 transposase is used to prepare tagmented double-stranded cDNA. A second transposome, i.e., suicide transposome 165 of FIG. 1B, comprising free ME transposon sequences (i.e., no PCR adaptor sequences) and Ts-Tn5 transposase is used to "normalize" the cDNA library (i.e., remove more abundant sequences from the library).

Figure 8:
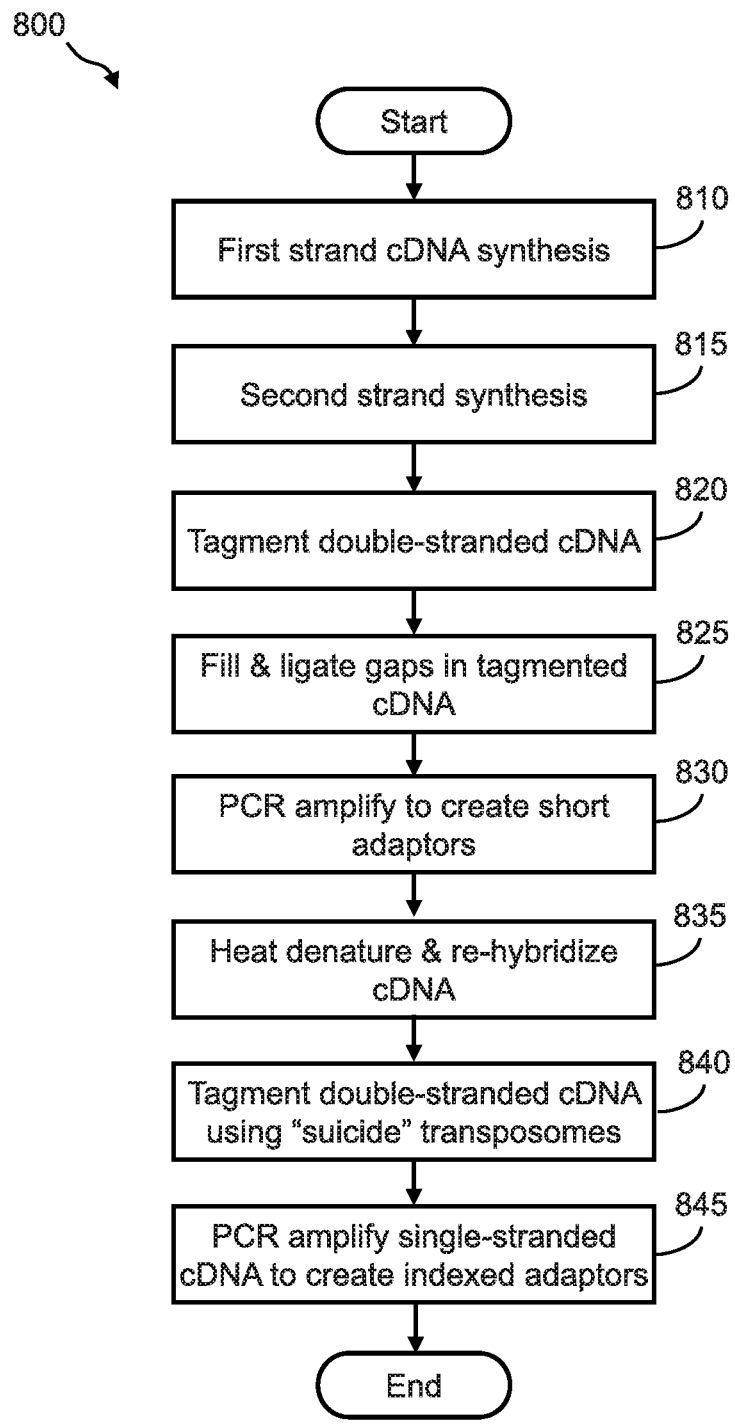
FIG. 8 illustrates a flow diagram of an example of a method of preparing and normalizing an RNA library for sequencing.
Figure 9:
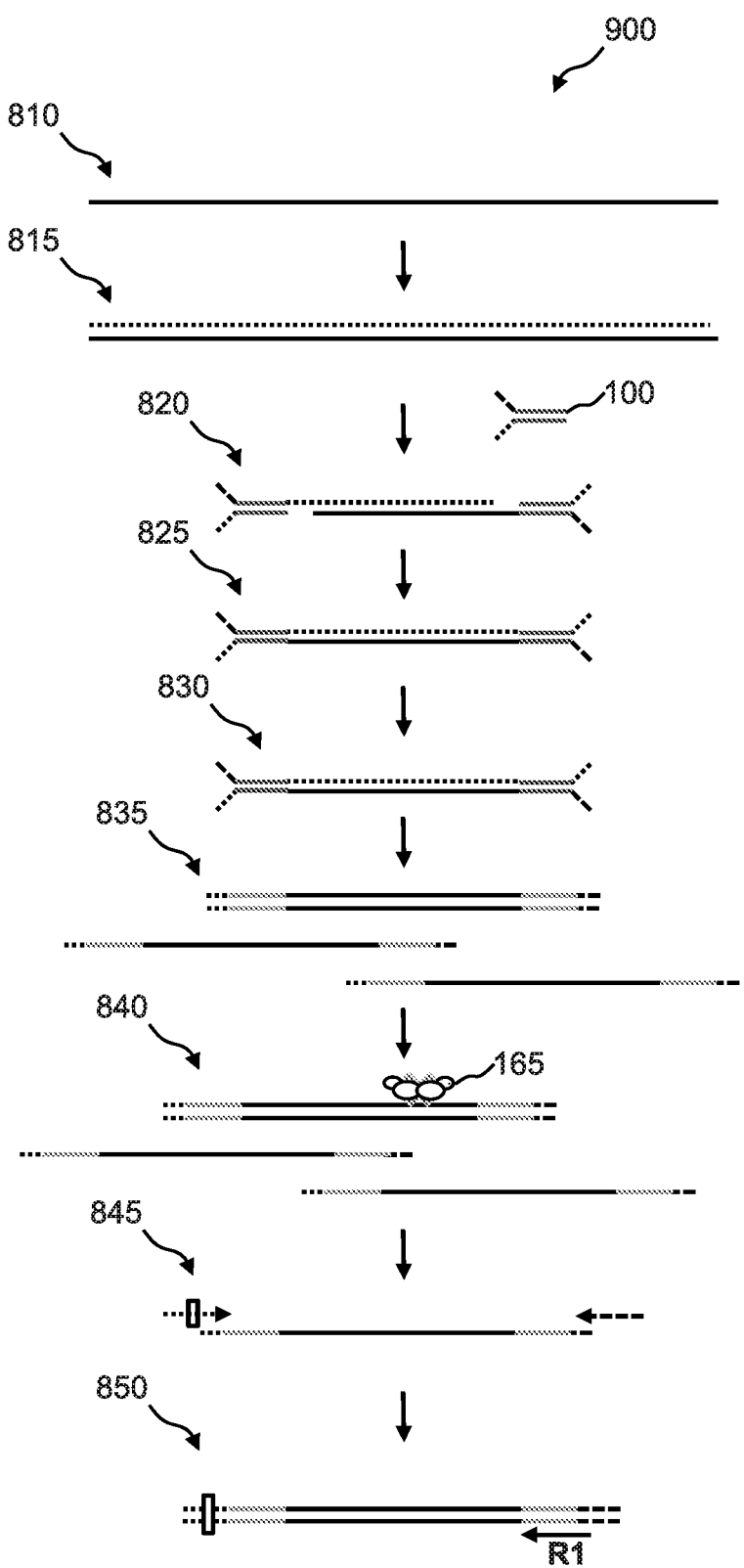
FIG. 9 illustrates a schematic diagram showing pictorially the steps of the method of FIG. 8.

FIG. 8 illustrates a flow diagram of an example of a method 800 of preparing and normalizing an RNA library for sequencing. FIG. 9 illustrates a schematic diagram 900 showing pictorially the steps of method 800 of FIG. 8. Referring now to FIG. 8, method 800 includes, but is not limited to, the following steps.

At a step 810, first strand cDNA is synthesized from total RNA. For example, a standard TotalScript™ first strand cDNA synthesis procedure using random hexamer primers and reverse transcriptase is used to reverse transcribe total RNA into first strand cDNA. This step is also shown pictorially in schematic diagram 900 of FIG. 9.

At a step 815, second strand cDNA is synthesized. For example, a standard TotalScript™ second strand synthesis procedure using UTP incorporation (instead of TTP) is used to synthesize the second cDNA strand. This step is also shown pictorially in schematic diagram 900 of FIG. 9.

At a step 820, double-stranded cDNA is tagmented using a forktail transposome to generate a library of fragments. The forktail transposome comprises forktail transposon 100 of FIG. 1A and Ts-Tn5 transposase. The library double-stranded cDNA fragments comprises abundant and less abundant sequences. A clean-up process (e.g., AMPure XP magnetic bead-based process) is performed to purify the tagmented DNA. This step is also shown pictorially in schematic diagram 900 of FIG. 9.

At a step 825, gaps in the cDNA formed in the transposition reaction are filled in and ligated. For example, a standard TotalScript™ gap fill/ligation reaction is used to fill-in and ligate 9 bp gaps on each strand of the tagmented cDNA. A clean-up process (e.g., AMPure XP magnetic bead-based process) is performed to purify the DNA. This step is also shown pictorially in schematic diagram 900 of FIG. 9.

At a step 830, the cDNA is PCR amplified to create short adaptor sequences. For example, PCR primers targeted to adaptor sequences 115 of forktail transposon 100 and Phusion® DNA polymerase (New England BioLabs) are used to amplify the first cDNA strand. PCR primers targeted to adaptor sequences 115 are limited to the adaptor sequences and do not hybridize to the ME sequences 110 in forktail transposon 100. They partially overlap with the ME, but do not hyb to the entire ME The second cDNA strand synthesized using UTP is not copied (amplified) by the Phusion® polymerase. A clean-up process (e.g., AMPure XP magnetic bead-based process) is performed to purify the DNA. This step is also shown pictorially in schematic diagram 900 of FIG. 9.

At a step 835, the cDNA library is heat denatured and renatured in a library normalization process. For example, the cDNA library is heat denatured at about 95° C. for about 15 minutes and renatured at about 70° C. for about 4 hours to about 8 hours. The rate at which a particular sequence will reassociate is proportional to the number of copies of that sequence in the DNA sample. For example, highly-repetitive (abundant) sequence will reassociate rapidly, while complex sequences (less abundant) will reassociate more slowly. The cDNA library is now a mixture of single-stranded (less abundant) and double-stranded (abundant) DNA molecules. This step is also shown pictorially in schematic diagram 900 of FIG. 9.

At a step 840, double-stranded cDNA in the renatured reaction mixture is tagmented using suicide transposome complex 165 of FIG. 1B. For example, suicide transposome 165 is added to the renatured reaction mixture and incubated at 70° C. for about 5 minutes. Renatured double-stranded DNA (e.g., from rRNA) is fragmented in the tagmentation reaction. Because the Ts-Tn5 suicide transposomes do not include adaptor sequences, the tagmented DNA is not amplified in subsequent process steps. Single-stranded DNA molecules (e.g., from lower abundance mRNAs) remain intact. A clean-up process (e.g., AMPure XP magnetic bead-based process) is performed to purify the DNA. This step is also shown pictorially in schematic diagram 900 of FIG. 9.

At a step 845, single-stranded cDNA is PCR amplified to create longer indexed adaptors. For example, adaptor sequences 115 are extended in the PCR reaction to comprise the remaining P5 and P7 primer sequences and an index sequence used for sequencing. The tagmented double-stranded cDNA is not PCR amplified. This step is also shown pictorially in schematic diagram 900 of FIG. 9.

At step 850, cDNA is PCR amplified to create the final library. Method 800 ends. This step is also shown pictorially in schematic diagram 900 of FIG. 9.

Throughout the process steps of method 800, the abundant sequences in the library (e.g., from rRNA) are retained in the reaction mixture. The abundant sequences may act as bulk carrier material to minimize sample loss (e.g., non-specific binding to reaction surfaces) during the processing steps.

Method 800 provides for library preparation (step 810 through step 830) in about 6 hours, library denaturation and renaturation (step 835) in about 4 to about 8 hours (or overnight), and library normalization (step 840 through step 850) in about 3 hours. In one example, method 800 is used for preparation of a normalized RNA-seq library from about 50 pg to about 500 pg of input RNA.

To evaluate the effect of library normalization on library output and sequencing metrics, cDNA libraries were prepared using universal human reference RNA and method 800 of FIG. 8. Table 1 shows the sample designation, sample name and description of 8 RNA-seq libraries prepared without normalization ("NoNorm") or with suicide-transposome normalization ("Norm"). Control libraries (i.e., libraries that were prepared without normalization) are designated by 582_1000 "NoNorm_A" and 582_2000 "NoNorm_B". Libraries that were prepared using suicide-transposome normalization are designated by "Norm_library input (ng)_transposome input (pmol)_duplicate". For example, the sample designated 582_3000 is named Norm50 ng_12 p_1 and represents a first library prepared using 50 ng of library input and 12.5 pmol suicide-transposome (TSM). The sample designated 582_4000 is named Norm50 ng_12 p_2 and represents a second library prepared using 50 ng of library input and 12.5 pmol TSM. The sample designated 582_5000 is named Norm100 ng_25 p_1 and represents a first library prepared using 100 ng of library input and 25 pmol TSM. The sample designated 582_6000 is named Norm100 ng_25 p_2 and represents a second library prepared using 100 ng of library input and 25 pmol TSM. The sample designated 582_7000 is named Norm50 ng_25 p_1 and represents a first library prepared using 50 ng of library input and 25 pmol TSM. The sample designated 582_8000 is named Norm50 ng_25 p_2 and represents a second library prepared using 50 ng of library input and 25 pmol TSM. All normalization reactions were performed using 1× normalization buffer and a renaturation and tagmentation temperature of 68° C.

TABLE 2

RNA-seq library sample designation, name and descriptions

| Sample Designation | Sample Name | Description |
| --- | --- | --- |
| 582_1000 | NoNorm_A | Control, Not Normalized |
| 582_2000 | NoNorm_B | Control, Not Normalized |
| 582_3000 | Norm50ng_12p_1 | 50 ng Lib, 12.5 pmol TSM, 1x Norm. buffer; 68° C. |
| 582_4000 | Norm50ng_12p_2 | 50 ng Lib, 12.5 pmol TSM, 1x Norm. buffer; 68° C. |
| 582_5000 | Norm100ng_25p_1 | 100 ng Lib, 25 pmol TSM, 1x Norm. buffer; 68° C. |
| 582_6000 | Norm100ng_25p_2 | 100 ng Lib, 25 pmol TSM, 1x Norm. buffer; 68° C. |
| 582_7000 | Norm50ng_25p_1 | 50 ng Lib, 25 pmol TSM, 1x Norm. buffer; 68° C. |
| 582_8000 | Norm50ng_25p_2 | 50 ng Lib, 25 pmol TSM, 1x Norm. buffer; 68° C. |

Figure 10:
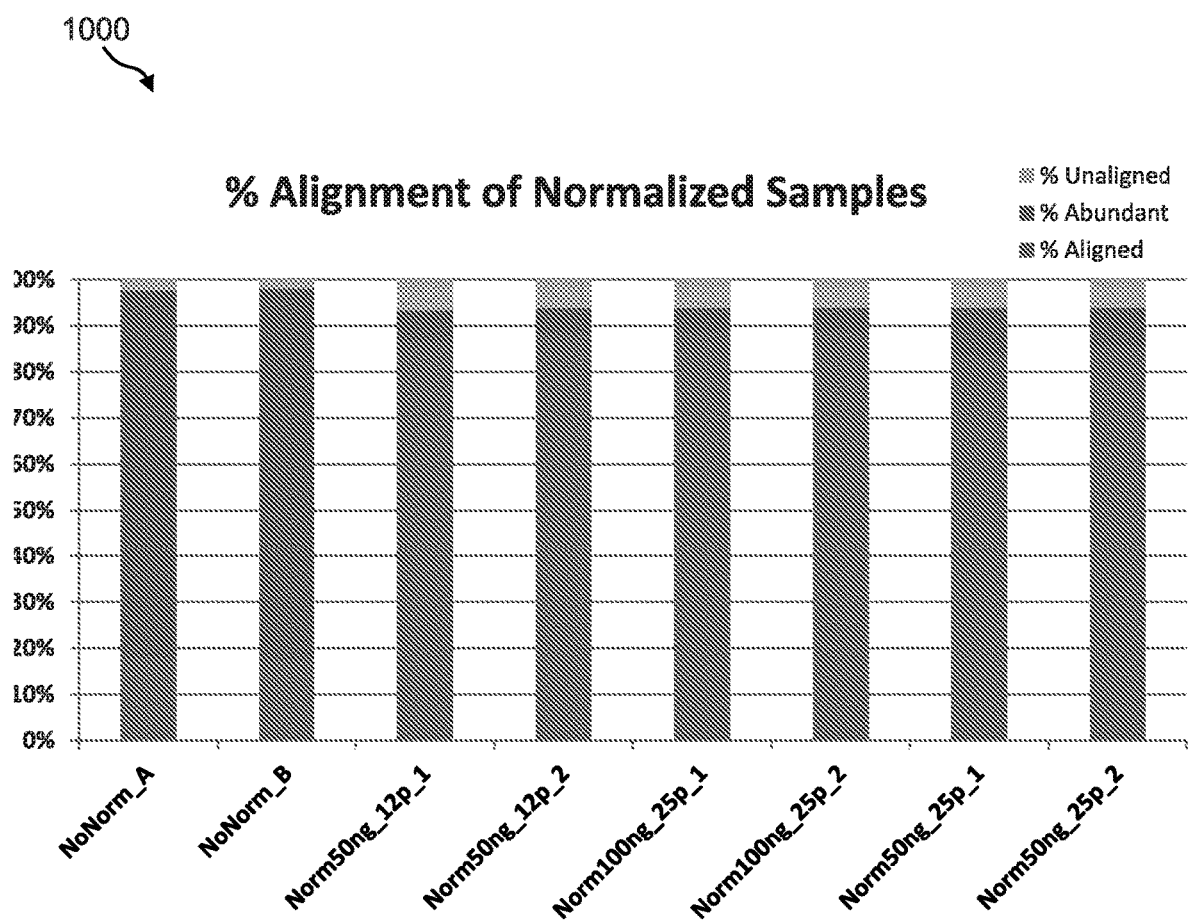
FIG. 10 shows a bar graph of the percent sequence alignment of control and suicide-transposome normalized libraries of Table 2, % aligned means alignment to genome, including known transcripts, non-coding RNA and intergenic sequence.

FIG. 10 shows a bar graph 1000 of the percent sequence alignment of control and suicide-transposome normalized libraries of Table 2. Each bar on the graph represents an RNA-seq library and shows the percent (%) aligned reads that represent normal transcripts (i.e., mRNA), % abundant reads that represent rRNA and mitochondrial RNA, and % unaligned that represent material that typically does not align in an RNA-seq experiment. The data show that all normalized samples (i.e., 582_300 through 582_800) have a substantially higher percentage of aligned reads (about 85%) and a corresponding decrease in percentage of abundant reads compared to control (i.e., not normalized) libraries.

Figure 11:
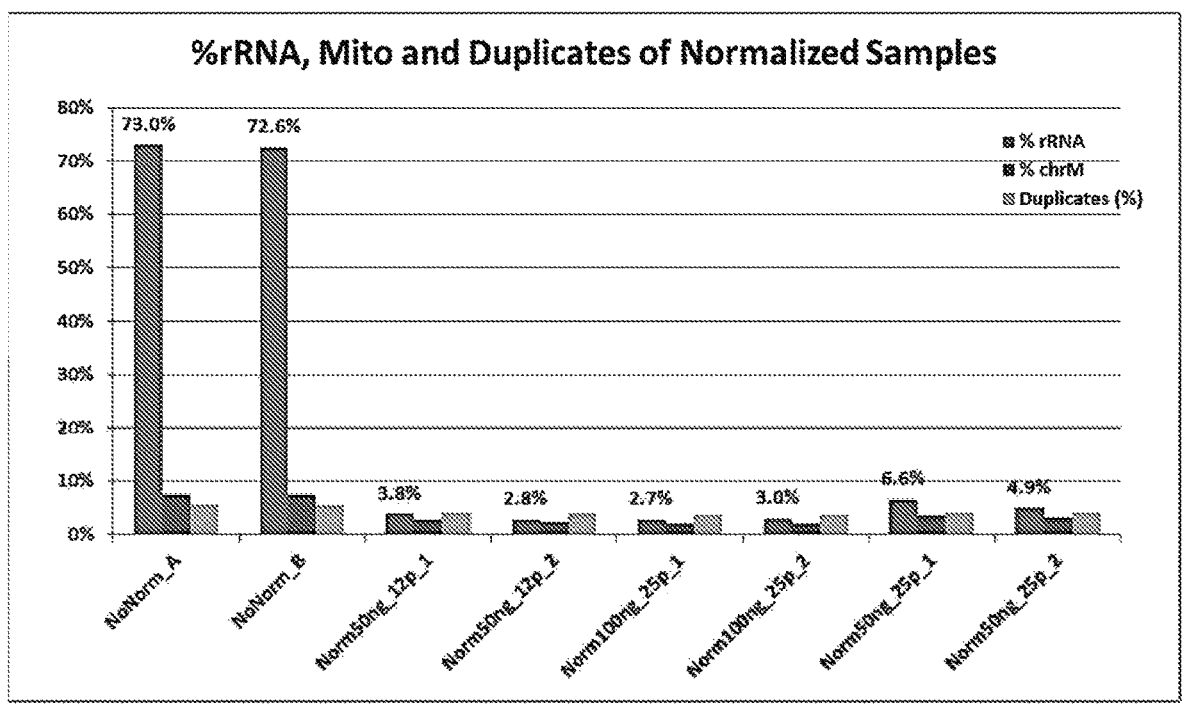
FIG. 11 shows a bar graph of the percent rRNA, mitochondrial RNA and duplicate reads in the abundant sequence fraction of samples of FIG. 10.

FIG. 11 shows a bar graph 1100 of the percent rRNA, mitochondrial RNA and duplicate reads in the abundant sequence fraction of samples shown in bar graph 1000 of FIG. 10. The data show that most of the abundant sequence fraction in control libraries is rRNA (i.e., about 73% of reads are rRNA). In normalized libraries, the percentage of reads from rRNA is from about 2 to about 6%.

Figure 12:
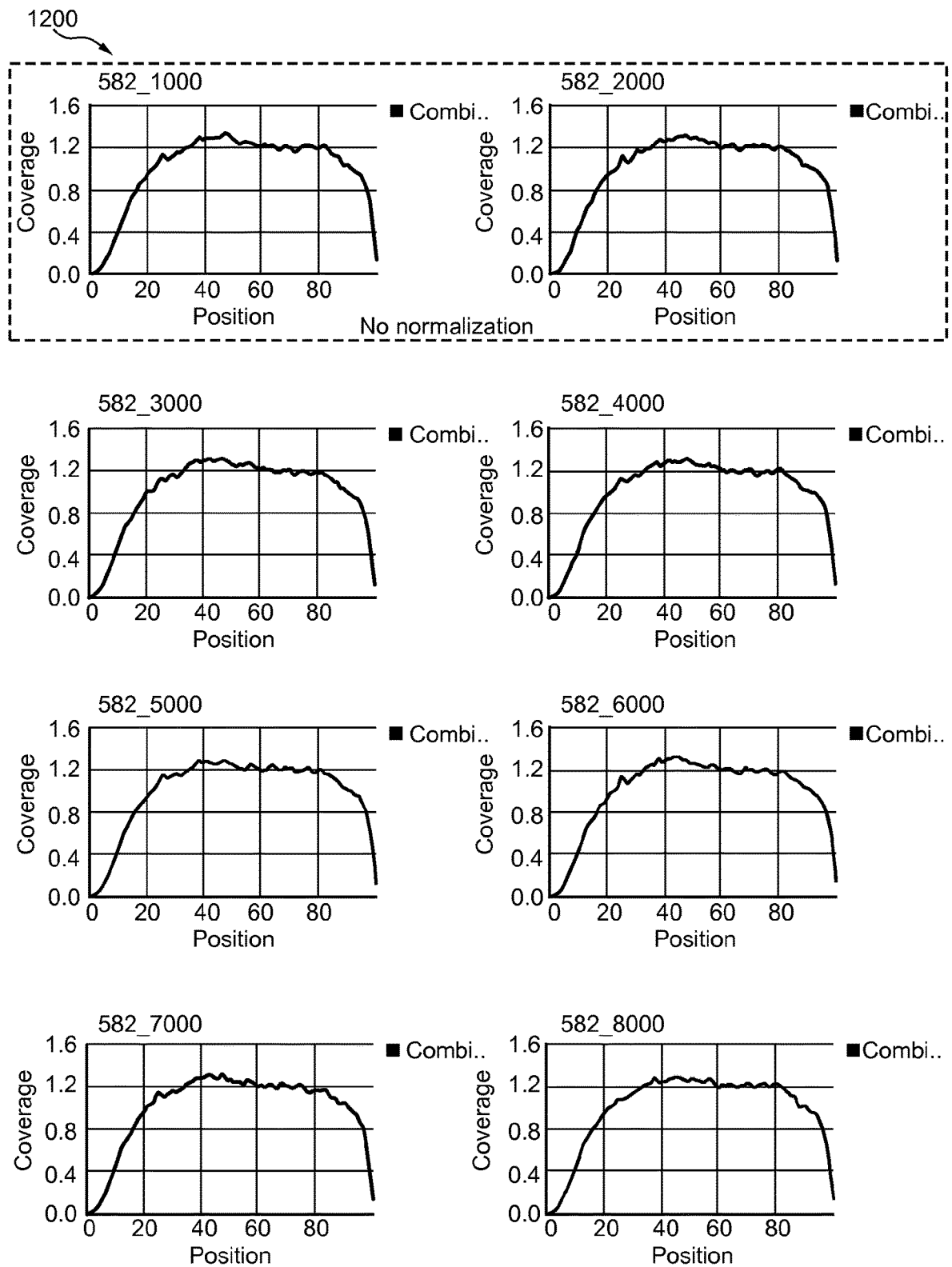
FIG. 12 shows a panel of the read distributions in control and suicide-transposome normalized libraries of Table 2.

FIG. 12 shows a panel 1200 of the read distributions in control and suicide-transposome normalized libraries of Table 2. The data show that the coverage across transcripts in the normalized libraries is about the same as the coverage in the control libraries.

Figure 13:
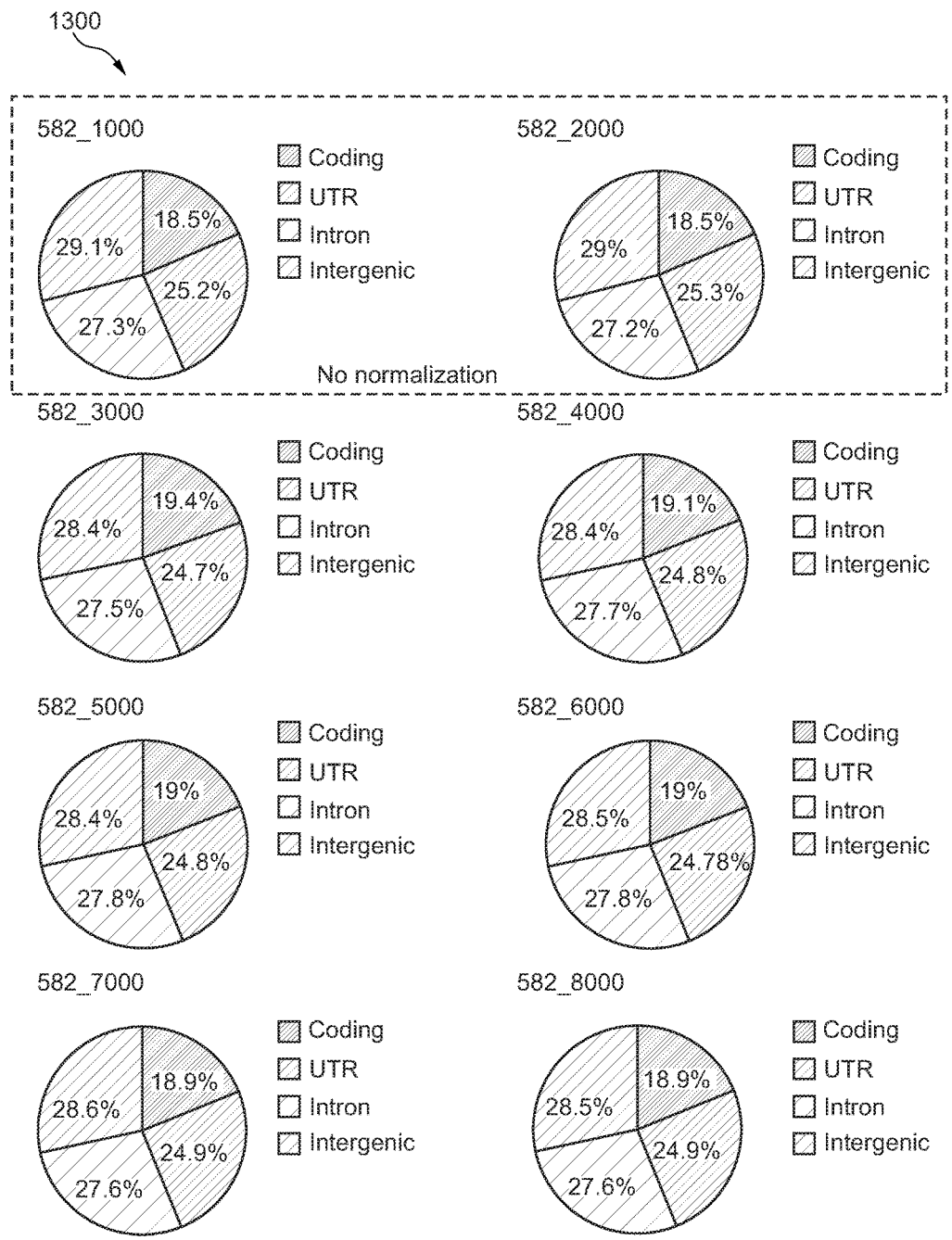
FIG. 13 shows a panel of the alignment locations in control and suicide-transposome normalized libraries of Table 2.

FIG. 13 shows a panel 1300 of the alignment locations in control and suicide-transposome normalized libraries of Table 2. The data show that the distribution of reads across categories (i.e., coding, UTR, Intron, and Intergenic) in the normalized libraries is about the same as the distribution in the control libraries.

Referring now to FIGS. 10 through 13, the data show that the transposome-mediated normalization process substantially removes rRNA, but not sequences across other RNA categories (e.g., coding, UTR, intron, and intergenic sequences).

Correlations are commonly calculated for RNA-seq data to check expression values and trends between samples. For example technical or biological replicates are expected to be closely correlated, i.e., have similar expression values for transcripts between two samples. Correlation value falls between 0 and 1, wherein 1 is directly correlated, 0 is not correlated at all. Table 3 shows the data set correlation for the control (Ctrl_1 and Ctrl_2) and normalized libraries of FIG. 11.

TABLE 3

Data set correlation

Subset Data - fpkm* in both pair has to be 1 or greater, Spearman Cor, r2

| | | | | | | | |
|---|---|---|---|---|---|---|---|
| Ctrl_1 | 1.00 | | | | | | |
| Ctrl_2 | 0.93 | 1.00 | | | | | |
| Norm50ng12p_1 | 0.93 | 0.92 | 1.00 | | | | |
| Norm50ng12p_2 | 0.93 | 0.92 | 0.94 | 1.00 | | | |
| Norm100ng25p_1 | 0.93 | 0.92 | 0.94 | 0.94 | 1.00 | | |
| Norm100ng25p_2 | 0.93 | 0.92 | 0.94 | 0.94 | 0.94 | 1.00 | |
| Norm50ng25p_1 | 0.93 | 0.92 | 0.93 | 0.93 | 0.94 | 0.93 | 1.00 |
| Norm50ng25p_2 | 0.93 | 0.91 | 0.93 | 0.93 | 0.93 | 0.93 | 0.92 | 1.00 |

Subset Data - fpkm* in both pair has to be 1 or greater, Pearson Cor, r2

| | | | | | | | |
|---|---|---|---|---|---|---|---|
| Ctrl_1 | 1.00 | | | | | | |
| Ctrl_2 | 0.95 | 1.00 | | | | | |
| Norm50ng12p_1 | 0.95 | 0.94 | 1.00 | | | | |
| Norm50ng12p_2 | 0.95 | 0.94 | 0.96 | 1.00 | | | |
| Norm100ng25p_1 | 0.95 | 0.94 | 0.96 | 0.95 | 1.00 | | |
| Norm100ng25p_2 | 0.95 | 0.94 | 0.96 | 0.96 | 0.96 | 1.00 | |
| Norm50ng25p_1 | 0.95 | 0.94 | 0.95 | 0.95 | 0.95 | 0.95 | 1.00 |
| Norm50ng25p_2 | 0.94 | 0.94 | 0.95 | 0.95 | 0.95 | 0.95 | 0.94 | 1.00 |

*fpkm = fragment per kilobase per million reads is a commonly used method to estimate abundance value In another application, a transposome-based library normalization method may be used in the analysis of nucleic acid from a single cell or a small group of cells (e.g., about 5 to 10 cells).

In another application, a transposome-based normalization method may be used to reduce the abundance of highly repetitive sequences in a plant genomic library.

In yet another application, a transposome-based library normalization method may be used to reduce abundant sequences in a metagenomics sample. In one example, a transposome-based normalization method may be used in a "de-hosting" application to deplete abundant host sequences (e.g., human rRNA or targeted human sequences) and enrich the pathogen (e.g., viral, bacterial, etc.) content in a clinical sample (e.g., infectious disease sample) or biological sample for sequencing.

In yet another application, a transposome-based normalization method may be used to reduce the number of duplicates in a Methyl-seq library.

4.5 Selective Capture of Nucleic Acids from a Mixture of Other Nucleic Acids or Other Impurities In one aspect, certain nucleic acids can be selectively captured from a mixture of other nucleic acids and other cellular components. In some embodiments, the nucleic acids that are selectively captured are purified from a mixture of nucleic acids and other cellular components. In some embodiments, certain nucleic acids are selectively purified from a mixture of nucleic acids and other cellular components by removing one or more type of other nucleic acids. In some embodiments, more than one type of nucleic acids can be selectively captured and/or purified from a mixture of nucleic acids or from a biological sample.

In some embodiments, the mixture of other nucleic acids may include or more of double stranded DNA, single stranded DNA, double stranded RNA, single stranded RNA, RNA-DNA hybrid, partially double stranded RNA or DNA.

In some embodiments, the nucleic acids to be selectively captured and/or purified can be double stranded DNA, single stranded DNA, RNA, double stranded RNA. In one preferred embodiment, the nucleic acids to be selectively purified are double stranded DNA. In one embodiment, the nucleic acids to be captured and/or purified are genomic DNA. In one embodiment, the nucleic acids to be selectively captured and/or purified have highly repetitive DNA or RNA sequences. In some embodiments, the nucleic acids to be selectively captured and/or purified may have multiple copies of the same sequence, for example, in polyploids.

In some embodiments, the nucleic acids to be selectively captured and/or purified from a biological sample. The biological sample can be any type that comprises the nucleic acids of interest. For example, the sample can comprise nucleic acids in a variety of states of purification, including purified nucleic acids. However, the sample need not be completely purified, and can comprise, for example, nucleic acids mixed with protein, other nucleic acid species, other cellular components and/or any other contaminant. In some embodiments, the biological sample comprises a mixture of nucleic acids of interest, protein, other nucleic acid species, other cellular components and/or any other contaminant present in approximately the same proportion as found in vivo. For example, in some embodiments, the components are found in the same proportion as found in an intact cell. In some embodiments, the biological sample has a 260/280 ratio of less than 2.0, 1.9, 1.8, 1.7, 1.6, 1.5, 1.4, 1.3, 1.2, 1.1, 1.0, 0.9, 0.8, 0.7, or less than 0.60. In some embodiments, the biological sample has a 260/280 ratio of at least 2.0, 1.9, 1.8, 1.7, 1.6, 1.5, 1.4, 1.3, 1.2, 1.1, 1.0, 0.9, 0.8, 0.7, or at least 0.60.

In some embodiments, specific types of nucleic acids (e.g., double stranded DNA, single stranded DNA, single stranded RNA, double stranded RNA, RNA-DNA hybrid, etc.) can be selectively captured and/or purified from a mixture of other nucleic acids or from a biological sample by using a nucleic acid binding protein immobilized on a solid support in which the protein binds selectively to the specific type of nucleic acids. In some embodiments, the nucleic acid binding protein immobilized on a solid support have enzymatic activity and require a cofactor. In some embodiments, the enzymatic activity may be a DNA altering activity such a nuclease activity, recombinase activity, ligase activity, kinase activity, gyrase activity, polymerase activity, transposase activity. In some embodiments, the nucleic acid binding protein immobilized on a solid support can bind to specific types of nucleic acids in the absence of cofactors.

In some embodiments, double stranded DNA can be selectively captured and/or purified from a mixture of other nucleic acids and/or from a biological sample using transposome complex immobilized on solid support, such as beads. Transposases of the immobilized transposome complex specifically recognize double stranded DNA as targets. In some embodiments, double stranded DNA binding proteins such as double-stranded exonucleases can be immobilized on a solid support and can be used to capture and purify double stranded DNA. The other nucleic acids such as RNA, single stranded DNA or any RND:DNA hybrids if any are not recognized by the immobilized transposomes or the double stranded DNA binding proteins. The use of preimmobilized transposomes or other double stranded DNA binding proteins on solid support allows better control by restricting the degree of freedom of transposome or other double stranded DNA binding proteins.

In some embodiments, the capture and purification of double stranded DNA can be carried out in the absence of divalent metal ions and in the presence of EDTA. In the absence of divalent mental ions, the preimmobilized transposomes on solid support will bind to the double stranded DNA but will not fragment it. The captured double stranded DNA bound to transposomes immobilized on a solid support can then be purified by removing it from the surrounding environment comprising other nucleic acids, cellular components, proteins, organelles, etc. In some embodiments, the captured double stranded DNA bound to the transposomes immobilized on a solid support can be removed from the surrounding environment by centrifugation. In some cases, the solid support comprise magnetic particles and the captured double stranded DNA bound to the transposomes immobilized on a solid support can be removed from the surrounding environment by the application of magnetic field. In some embodiments, the captured double stranded DNA bound to the transposomes immobilized on a solid support, in which the solid support is the wall of a tube or the flow cell, and the unbound nucleic acid such as single stranded DNA, RNA, RNA: DNA hybrid, excess double stranded DNA present in the surrounding environment are removed by washing the tube or the flow cell with wash buffer.

In some embodiments, more than one type of nucleic acid can be selectively captured and/or purified from a mixture of nucleic acids or from a biological sample. More than one type of nucleic acid binding protein immobilized on a solid support may be used to selectively capture more than one type of nucleic acid from a mixture of nucleic acids or from a biological sample.

In some embodiments, the methods can be further used to partially purify selective types of nucleic acids from a mixture of nucleic acids in a biological sample. For example, a specific type of nucleic acid can be selectively removed from a mixture of nucleic acids, such as, double stranded DNA, single stranded DNA, single stranded RNA, double stranded RNA, RNA-DNA hybrid, etc., thus unbound nucleic acids depleted of the bound nucleic acids are partially purified. In some embodiments, methods can be used for archiving unbound nucleic acids after selectively capturing and removing a specific type of nucleic acid.

In some aspects, presented herein are methods of preparing an immobilized library of tagged DNA fragments comprising: (a) providing a solid support having transposome complexes immobilized thereon, wherein the transposome complexes comprise a transposase bound to a first polynucleotide, the first polynucleotide comprising (i) a 3' portion comprising a transposon end sequence, and (ii) a first tag comprising a first tag domain; and (b) applying a target DNA to the solid support under conditions whereby the target DNA is fragmented by the transposome complexes, and the 3' transposon end sequence of the first polynucleotide is transferred to a 5' end of at least one strand of the fragments; thereby producing an immobilized library of double-stranded fragments wherein at least one strand is 5'-tagged with the first tag. The details of such methods are disclosed in US patent application publication 2014/0194324, which is incorporated by reference in its entirety.

In some embodiments, the selective capture and/or purification of a specific type of nucleic acid can be performed at an elevated temperature in which the nucleic acid binding protein immobilized on a solid support that binds selectively to the specific type of nucleic acids is stable at the elevated temperature. In some embodiments, the temperature can be raised and rapidly cooled down allowing the more abundant double stranded nucleic acids and the double stranded nucleic acids with highly repetitive sequences to anneal faster than other double stranded nucleic acids. These annealed nucleic acids then can be selectively captured and/or removed or purified. In some embodiments, the method can be used to remove polyploidy DNA.

5 REFERENCES

1. Britten R J and Kohne D E (1968) Repeated sequences in DNA. Science 161, 529-540.

6 CONCLUDING REMARKS

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

What is claimed is:

1. A method of analyzing rare nucleic acid species comprising:
   (a) providing a library of double-stranded nucleic acids;
   (b) denaturing the library;
   (c) renaturing the library under conditions sufficient to renature abundant nucleic acid species, wherein a portion of the library comprising less abundant nucleic acid species does not renature;
   (d) contacting the library with a transposase that preferentially binds to double-stranded nucleic acids; and
   (e) separating renatured abundant nucleic acid species from the less abundant nucleic acid species.

2. The method of claim 1, wherein separating comprises immobilizing the transposase to a solid support.

3. The method of claim 1, wherein the transposase comprises Tn5 or TS-Tn5 transposase.

4. The method of claim 1, wherein the transposase comprises adaptor sequences which comprise a binding moiety capable of binding to a solid support.

5. The method of claim 4, wherein the binding moiety comprises biotin and the solid support comprises streptavidin.

6. The method of claim 1, wherein the transposase comprises adaptor sequences which are not compatible with downstream amplification and sequencing.

7. The method of claim 1, wherein denaturing comprises heat denaturing.

8. The method of claim 1, wherein renaturing comprises lowering the denaturation temperature to a temperature of about 40° C. to about 65° C. for a sufficient period of time to renature abundant nucleic acid species.

9. The method of claim 1, wherein denaturing comprises chemical denaturing.

10. The method of claim 1, further comprising sequencing the separated less abundant nucleic acid species.

11. The method of claim 1, wherein the library comprises genomic DNA.

12. The method of claim 1, wherein the library comprises randomly sheared DNA.

13. The method of claim 1, wherein the library comprises double-stranded cDNA.

14. The method of claim 1, wherein the nucleic acids in the library comprise adaptor sequences ligated to the ends of the nucleic acids.

15. The method of claim 14, wherein the adaptor sequences comprise one or more of: amplification priming binding region, sequencing primer binding region, and promotor sequences for in vitro transcription.

16. The method of claim 1, wherein the abundant nucleic acid species comprise highly repetitive sequences.

17. The method of claim 1, wherein the library comprises nucleic acid from a single cell or a small group of cells.

18. The method of claim 1, wherein the abundant nucleic acid species comprise host sequences and the less abundant nucleic acid species comprise pathogen content.

19. The method of claim 1, wherein the library comprises genomic RNA.

\* \* \* \* \*